US012761201B2

(12) United States Patent
Ishiguro

(10) Patent No.: US 12,761,201 B2
(45) Date of Patent: Oct. 13, 2026

(54) CALCULATION DEVICE, CALCULATION METHOD, AND PROGRAM

(71) Applicant: RIKEN KEIKI CO., LTD., Tokyo (JP)

(72) Inventor: Tomoo Ishiguro, Kasukabe (JP)

(73) Assignee: RIKEN KEIKI CO., LTD. (JP)

( * ) Notice: Subject to any disclaimer, the term of this patent is extended or adjusted under 35 U.S.C. 154(b) by 346 days.

(21) Appl. No.: 18/287,137

(22) PCT Filed: Apr. 19, 2021

(86) PCT No.: PCT/JP2021/015847
§ 371 (c)(1),
(2) Date: Oct. 16, 2023

(87) PCT Pub. No.: WO2022/224297
PCT Pub. Date: Oct. 27, 2022

(65) Prior Publication Data
US 2024/0210373 A1 Jun. 27, 2024

(51) Int. Cl.
*G01N 21/45* (2006.01)
*G01N 33/22* (2006.01)

(52) U.S. Cl.
CPC ........... *G01N 33/225* (2013.01); *G01N 21/45* (2013.01)

(58) Field of Classification Search
CPC ............................. G01N 33/225; G01N 21/45
See application file for complete search history.

(56) References Cited

U.S. PATENT DOCUMENTS 10,132,746 B2 11/2018 Kojima et al.
10,288,559 B2 * 5/2019 Muniraju ........... G01N 21/3518
10,816,413 B2 10/2020 Ishiguro et al.
11,193,917 B2 12/2021 Kojima et al.
(Continued)

FOREIGN PATENT DOCUMENTS

CN 107636451 A 1/2018
CN 111328372 A 6/2020
(Continued)

OTHER PUBLICATIONS

Computer translation of WO_2020/148927_A1 (Year: 2025).*
(Continued)

*Primary Examiner* — Randy W Gibson
(74) *Attorney, Agent, or Firm* — Harness, Dickey & Pierce, P.L.C.

(57) ABSTRACT

A calculation device is configured to calculate a value relating to a combustible target gas containing miscellaneous gas components. The calculation device includes: a heating value calculation unit configured to calculate a heating value of the target gas on the basis of converted heating values obtained from a refractive index and a density of the target gas, respectively; a miscellaneous gas total approximate-concentration calculation unit configured to calculate an approximate concentration of the miscellaneous gas components on the basis of the converted heating values; and a virtual basic-heating-value calculation unit configured to calculate, on the basis of the heating value and the approximate concentration, a virtual basic heating value of the target gas when the miscellaneous gas components are assumed to be removed.

20 Claims, 17 Drawing Sheets

(56) References Cited

U.S. PATENT DOCUMENTS

| | | | | |
|---|---|---|---|---|
| 2011/0015874 | A1* | 1/2011 | Song | G01N 21/774 250/573 |
| 2014/0104613 | A1* | 4/2014 | Birnkrant | G01N 21/0303 356/402 |
| 2017/0115246 | A1* | 4/2017 | Herb | G01N 25/30 |
| 2017/0370831 | A1 | 12/2017 | Kojima et al. | |
| 2018/0180493 | A1 | 6/2018 | Ishiguro et al. | |
| 2021/0262996 | A1 | 8/2021 | Kojima et al. | |
| 2022/0074850 | A1* | 3/2022 | Plemmons | G01N 21/3504 |

FOREIGN PATENT DOCUMENTS

| | | | |
|---|---|---|---|
| JP | 2010-175261 | A | 8/2010 |
| JP | 2013-057532 | A | 3/2013 |
| JP | 6402387 | B2 | 10/2018 |
| JP | 2021-004891 | A | 1/2021 |
| WO | 2016-104270 | A1 | 6/2016 |
| WO | 2017013897 | A1 | 1/2017 |
| WO | 2020148927 | A1 | 7/2020 |

OTHER PUBLICATIONS

Naoki Nakamura, "Development and verification results of optsonic calorimeter to solve on-site problems", Instrumentation, Nov. 1, 2014, 7 pages.

Matsushita Takuro et al., "Field instrumentation tool pursuing on-site needs—Development aim and operation", Development/ introduction examples, Calorific value measurement technology that eliminates the effects of miscellaneous gas components, Instrumentation, May 1, 2010, 15 pages.

International Search Report of the International Searching Authority, issued in PCT/JP2021/015847, mailed Jul. 6, 2021; ISA/JP (6 pages).

European Search Report issued in the corresponding European Patent Application No. 21937796.7; dated Dec. 12, 2024 (total 10 pages).

Office Action issued in the corresponding Chinese Patent Application No. 202180097274.5; issued Dec. 29, 2025 (total 13 pages).

* cited by examiner

CALCULATION DEVICE, CALCULATION METHOD, AND PROGRAM

CROSS REFERENCE TO RELATED APPLICATIONS

This application is a 371 U.S. National Phase of International Application No. PCT/JP2021/015847, filed on Apr. 19, 2021. The entire disclosure of the above application is incorporated herein by reference.

BACKGROUND

Technical Field

The present invention relates to a calculation device, a calculation method, and a program that can calculate various values relating to combustion of a target gas (for example, a natural gas).

Related Art

For the handling of combustible gases, there are many physical property values that serve as an index or a standard, and various calculation methods are used for each physical property value.

One of the physical property values of combustible gases is a heating value. Among the methods of measuring the heating value, there has been known a method in which the heating value of a target gas, which is the gas subjected to heating value measurement, is calculated on the basis of a refractive index-converted heating value that is obtained from the refractive index of the target gas and on a sound speed converted-heating value obtained from the sound speed of the target gas (see, for example, Japanese Patent No. 6402387).

Examples of other physical property values include a compression factor and a combustion speed. To calculate these values, methods that conform to international standards are generally used. In this case, for example, composition analysis values of gas chromatography are generally used as input values (parameters).

For calculating the compression factor of a natural gas, methods according to ISO12213-2 and ISO12213-3 are widely known, for example.

The calculation method according to ISO12213-2 is a method of calculating a compression factor Z using a pressure P and a temperature T of a natural gas, and a molar concentration xi of each component that composes the natural gas as input values (input parameters).

The calculation method according to ISO12213-3 uses a pressure P and a temperature T of a natural gas, a heating value Hs (a gross heating value converted to a measurement reference state temperature of 0° C., a combustion reference state of 25° C., and 101.325 kPa), a specific gravity d, a carbon dioxide concentration $x_{CO2}$, and a hydrogen concentration $x_{H2}$ as input parameters to calculate a large number of items as intermediate data, the items including a molar fraction $x_{CH}$ of a hydrocarbon gas, a molar fraction $x_{N2}$ of nitrogen, a molar fraction $x_{CO}$ of carbon monoxide, a molar heating value $H_{CH}$ of an equivalent hydrocarbon gas, a molar mass $M_{CH}$ of an equivalent hydrocarbon gas, a second virtual conversion coefficient (Tn=273.15 K) Bn, a molar density ρm, n under standard conditions, a mass density ρn under standard conditions, and a total heating value Hs. After the calculation, the compression factor Z is calculated using these intermediate data.

In general, a combustion speed MCP of city gas is typically calculated from the composition analysis values of gas chromatography using a (Pa) formula shown below.

$$MCP = (1 - K) \times \{\Sigma(Si \bullet fi \bullet Ai)\} / \{\Sigma(fi \bullet Ai)\} \quad \text{(Pa)}$$

Si: combustion speed of flammable gas component i in the gas fi: factor relating to each flammable gas component i in the gas Ai: volume percentage of each flammable gas component i in the gas K: attenuation factor with a value calculated by the following equation:

$$K = \left\{\sum Ai \Big/ \left(\sum \alpha i \cdot Ai\right)\right\} \times \left\{ \begin{array}{r} (2.5CO_2 + N_2 - 3.77O_2)/(100 - 4.77O_2) + \\ {[(N_2 - 3.77O_2)/(100 - 4.77O_2)]^2} \end{array} \right\}$$

αi: correction coefficient for flammable gas component i in the gas $CO_2$, $N_2$, $O_2$: volume percentage of each component in the gas However, for different physical property values (for example, a compression factor, and a combustion speed), parameters used for their calculations are often different from one another, necessitating the use of methods for acquiring the respective parameters. Naturally, when a large number of parameters are used as in the case of calculating the compression factor, the procedures and devices involved in the calculation become complicated.

In the case of the compression factor in particular, the pressure P and the temperature T are used as initial input data in the calculation methods according to ISO12213-2 and ISO12213-3. However, under conditions of different temperatures and pressures, it is necessary to re-calculate starting from all of the input data required for the respective calculation methods in order to calculate the compression factor. This necessity causes a problem of inconvenience. Also there is a problem in that when the temperature or pressure is not measurable, numerical values relating to the compression factor cannot be acquired.

These problems also exist in the calculation of other physical property values (for example, the combustion speed). The combustion speed in particular is calculated using the analytical values of a gas chromatography device, which is a large and expensive device. As a result, the calculation is costly and is not easily performed.

Thus, pertaining to the calculation of a plurality of types of physical property values in particular, studies on simple and relatively low-cost means and techniques have not made significant progress so far.

The present invention has been made in view of the above-described problems, and it is an object of the present invention to provide a calculation device, a calculation method, and a program that can perform easy and relatively low-cost calculation of a plurality of types of physical property values relating to combustion gases.

SUMMARY

The present invention relates to a calculation device configured to calculate a value relating to a combustible target gas containing miscellaneous gas components, the calculation device including: a heating value calculation unit configured to calculate a heating value of the target gas on the basis of converted heating values obtained from a refractive index and a density of the target gas, respectively; a miscellaneous gas total approximate-concentration calculation unit configured to calculate a total approximate concentration of the miscellaneous gas components on the basis of the converted heating values; and a virtual basic-heating-value calculation unit configured to calculate, on the basis of the heating value and the approximate concentration, a basic heating value of the target gas when the miscellaneous gas components are assumed to be removed (hereinafter referred to as a "virtual basic heating value").

The present invention also relates to a calculation method of calculating a value relating to a combustible target gas containing miscellaneous gas components, the calculation method including: a step of acquiring converted heating values obtained from a refractive index and a density of the target gas, respectively; a step of calculating a heating value of the target gas on the basis of the converted heating values; a step of calculating a total approximate concentration of the miscellaneous gas components on the basis of the converted heating values; and a step of calculating, on the basis of the heating value and the total approximate concentration, a basic heating value of the target gas when the miscellaneous gas components are assumed to be removed (hereinafter referred to as a "virtual basic heating value").

The present invention also relates to a program for causing a computer to execute the calculation method described above. The program is generally stored in a RAM or a ROM of the computer. Thus, the program is in the form of a non-transitory computer readable medium.

Advantageous Effects of Invention

The present invention can provide a calculation device, a calculation method, and a program that can perform easy and relatively low-cost calculation of a plurality of types of physical property values relating to combustion gases.

DETAILED DESCRIPTION

Figure 1:
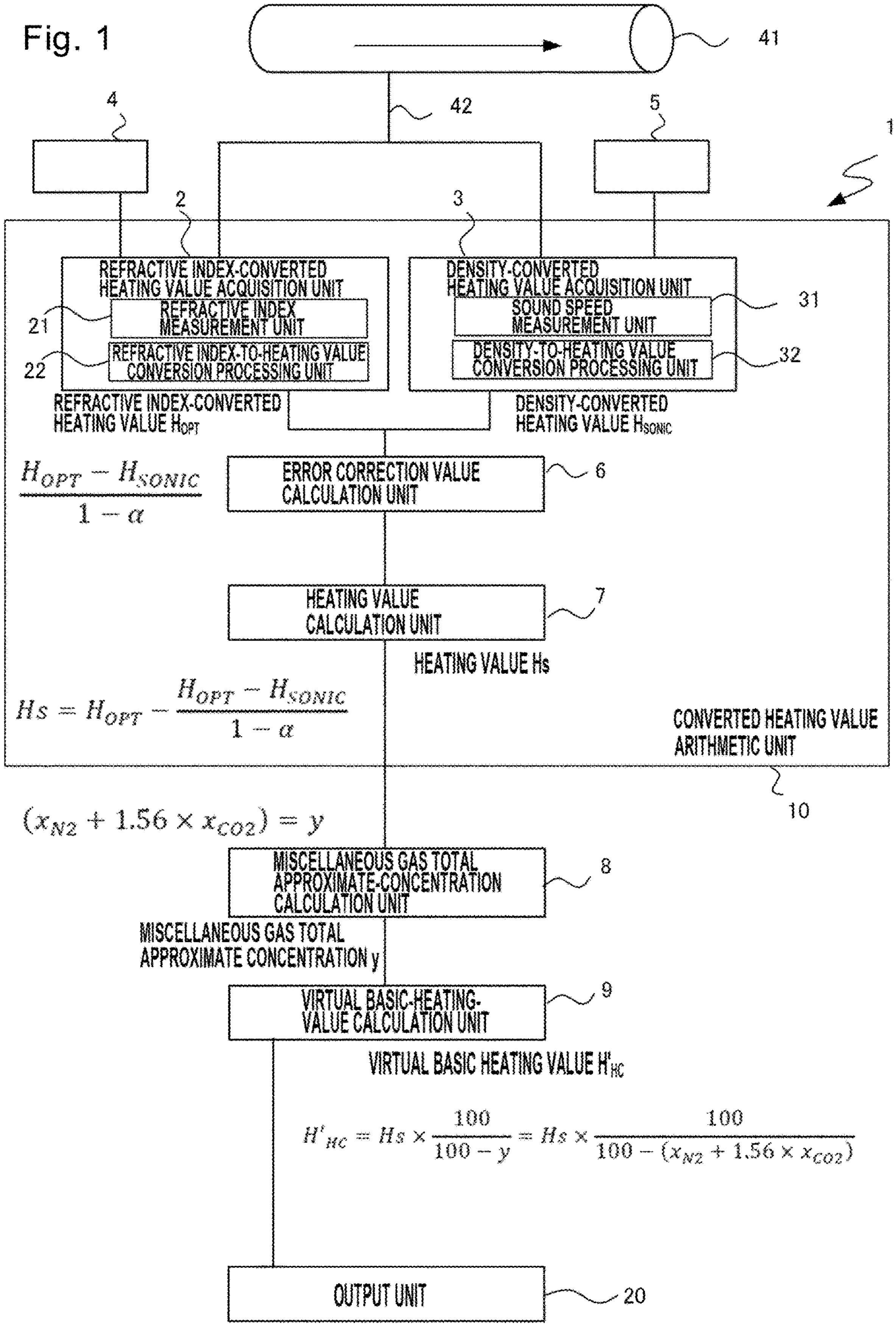
FIG. 1 is a block diagram showing an example of a calculation device according to a present embodiment.

Embodiments of the present invention will be described below with reference to the accompanying drawings. First, a calculation device 1 according to an embodiment of the present invention is a device configured to calculate a value relating to a combustible target gas containing miscellaneous gas components. Here, examples of the "value relating to the combustible target gas" in the present embodiment include values (physical property values, and factors) relating to the combustion of the target gas (combustible gas), and values (physical property values, and factors) relating to the states of the combustible gas. Here, a description will be given of the case where, for example, the value (physical property values, and factors) relating to the combustion of combustible gas is a basic heating value or a value relating to the basic heating value or a combustion speed, and the value (physical property values, and factors) relating to the states of the combustible gas is a value relating to the compression factor.

The target gas of the present embodiment is a natural gas that is just produced from gas fields or a biogas. Examples of the target gas include a natural gas containing miscellaneous gas (noncombustible gas) components. Specifically, the target gas is a gas containing a first gas (a combustible gas) as a main component and a second gas (a miscellaneous gas, a noncombustible gas) that is a measurement error component. More specifically, examples of the first gas include paraffin-based hydrocarbon gases (for example, a methane gas ($CH_4$), an ethane gas ($C_2H_6$), a propane gas ($C_3H_8$), and a butane gas (n-$C_4H_{10}$), which have a specific correspondence relation between their heating values and refractive indexes and between their heating values and densities (specifically, the densities are proportional to the heating values, and the refractive indexes are proportional to the heating values).

The second gas is a gas as miscellaneous gas components, which has no specific correspondence relation between its heating value and its refractive index and between its heating value and its density. For example, the miscellaneous gas components are a gas mainly containing (a mixture of) nitrogen ($N_2$) and carbon dioxide ($CO_2$). The "gas mainly containing nitrogen (N2) and carbon dioxide (CO2)" is a gas that does not contain noncombustible gas components other than N2 and CO2 or combustible gas (such as a hydrogen gas and a carbon monoxide gas) components other than paraffin-based hydrocarbon gases or that contains a very small amount of above gas components that are small enough to be negligible in terms of the calculation error.

The heating value Hs of a natural gas in the following description is standardized as a gross heating value MJ/$m^3$ (measurement reference state temperature of 0° C., combustion reference state of 0° C., 101.325 kPa). The units of concentration of various gases are standardized as molar concentration [mol %].

<Calculation Device>

FIG. 1 is a block diagram schematically showing an example of the configuration of the calculation device 1 according to a first embodiment. For example, the calculation device 1 of the present embodiment is a device configured to calculate values relating to the target gas that circulates through a gas pipeline 41 in the direction of an arrow in FIG. 1. The calculation device 1 includes a converted heating value arithmetic unit 10, a miscellaneous gas total approximate-concentration calculation unit 8, a virtual basic-heating-value calculation unit 9, and an output unit 20.

The converted heating value arithmetic unit 10 includes a refractive index-converted heating value acquisition unit 2, a density-converted heating value acquisition unit 3, an error correction value calculation unit 6, and a heating value calculation unit 7. The converted heating value arithmetic unit 10 is a unit configured to arithmetically operate and output a heating value (converted heating value) of the target gas while taking into account the error caused by miscellaneous gas components. This arithmetic occurs on the basis of a converted heating value that is converted from a refractive index of the target gas (including miscellaneous gas components) and a converted heating value that is converted from density.

The gas pipeline 41 is connected to the refractive index-converted heating value acquisition unit 2 and the density-converted heating value acquisition unit 3 through a gas flow channel 42, and the target gas in the gas pipeline 41 is thus supplied to the refractive index-converted heating value acquisition unit 2 and the density-converted heating value acquisition unit 3. For example, the calculation device 1 is disposed inside an explosion-proof container (not shown).

The refractive index-converted heating value acquisition unit 2 is a device (for example, an interferometer, a refractive index calorimeter, etc.) configured to detect, for example, a difference in the refractive index of light between the target gas and a standard gas such as air. This difference is detected as a displacement of interference fringes, and the detection occurs on the basis of an output signal (a voltage applied to the refractive index-converted heating value acquisition unit 2) from an external device (such as a power source device) 4. Based on the displacement amount of the interference fringes, a refractive index-converted heating value $H_{OPT}$ of the target gas is acquired.

For example, the refractive index-converted heating value acquisition unit 2 includes a refractive index measurement unit 21 (for example, a light sensor) configured to measure the refractive index of the target gas, and a refractive index-to-heating value conversion processing unit 22 having a function of obtaining the refractive index-converted heating value $H_{OPT}$ on the basis of the value of the refractive index measured by the refractive index measurement unit 21.

The refractive index-to-heating value conversion processing unit 22 has a prescribed correlation expression based on the refractive index and the heating value acquired in advance for gases (gases not containing miscellaneous gas components) composed only of the combustible gas components that serve as standards (paraffin-based hydrocarbon gases). The refractive index-to-heating value conversion processing unit 22 then calculates the refractive index-converted heating value $H_{OPT}$ of the target gas by applying the value of the actually measured refractive index of the target gas to the correlation expression. This calculation is made with the assumption that the value of the actually measured refractive index of the target gas is the refractive index of the combustible gas.

For example, the density-converted heating value acquisition unit 3 is a device configured to measure the sound speed of the target gas on the basis of an output signal (a voltage applied to the density-converted heating value acquisition unit 3) from an external device (such as a power supply unit) 5 to acquire a density-converted heating value $H_{SONIC}$ of the target gas.

The density-converted heating value acquisition unit 3 includes a sound speed measurement unit (for example, a sound speed sensor) 31 configured to measure propagation speed of sound waves in the target gas (the sound speed of the target gas), and a density-to-heating value conversion processing unit configured to calculate the density of the target gas on the basis of the sound speed measured by the sound speed measurement unit 31 to obtain the density-converted heating value $H_{SONIC}$.

The density-to-heating value conversion processing unit has a prescribed correlation expression based on the density (sound speed) and the heating value acquired in advance for gases (gases not containing miscellaneous gas components) composed only of the combustible gas components that serve as standards (paraffin-based hydrocarbon gases). The density-to-heating value conversion processing unit calculates the density-converted heating value $H_{SONIC}$ of the target gas by applying the value of the actually measured density of the target gas to the correlation expression on the assumption that the actually measured value of the density is the density of the combustible gas.

The error correction value calculation unit 6 calculates a value (an error correction value: a second term of the right side of the formula (7) described later) that corrects an error (an error caused by miscellaneous gases) in the calculation of the heating value, the error being caused by the miscellaneous gases (a nitrogen gas and a carbon dioxide gas) contained in the target gas.

The heating value calculation unit 7 is a unit that has a converted heating value arithmetic formula (the formula (7) described later) and is configured to calculate a heating value Hs of the target gas. This calculation is performed by a prescribed arithmetic operation on the basis of converted heating values obtained from the refractive index and the density of the target gas (the refractive index-converted heating value $H_{OPT}$ and the density-converted heating value $H_{SONIC}$), respectively, and on the basis of the error correction value. The prescribed arithmetic operation is an arithmetic operation (arithmetic operation of a converted heating value) uniquely developed by the applicant of the present invention. The arithmetic operation is hereinafter referred to as Opt-Sonic arithmetic operation.

The miscellaneous gas total approximate-concentration calculation unit 8 is a unit, having a miscellaneous gas total approximate-concentration calculation formula (the formula (8) described later), configured to calculate a total approximate concentration of the miscellaneous gas components in the target gas (a miscellaneous gas total approximate concentration y) on the basis of the refractive index-converted heating value $H_{OPT}$ and the density-converted heating value $H_{SONIC}$. The target gas handled in the present embodiment mainly contains a nitrogen gas and a carbon dioxide gas as miscellaneous gas components. Even when the individual concentrations of these gases are unknown, the concentrations are replaced with a total concentration that allows an approximation error, and various arithmetic operations are performed with the total concentration. The total concentration of the miscellaneous gases that allows an approximation error is the miscellaneous gas total approximate concentration y. The miscellaneous gas total approximate-concentration calculation unit 8 can calculate the total approximate concentration of the miscellaneous gas components (a nitrogen gas and a carbon dioxide gas) (the miscellaneous gas total approximate concentration y) on the basis of the refractive index-converted heating value $H_{OPT}$ and the density-converted heating value $H_{SONIC}$.

The virtual basic-heating-value calculation unit 9 has a virtual basic-heating-value calculation formula (the formula (9) described later). When the concentration of miscellaneous gases (a nitrogen gas and a carbon dioxide gas) is unknown, the virtual basic-heating-value calculation unit 9 assumes that the total concentration of the miscellaneous gases is the miscellaneous gas total approximate concentration y. Then, the virtual basic-heating-value calculation unit 9 obtains by arithmetic operation a basic heating value $H'_{HC}$(i.e., a heating value of only the combustible gas component in the target gas) of the target gas when the miscellaneous gas components based on the assumption are removed.

Here, the "basic heating value" of the target gas refers to the heating value when the target gas is composed only of combustible gases (paraffin-based hydrocarbon gases). When the target gas contains miscellaneous gas components, they are removed and then the heating value is measured (calculated). Therefore (as will be described later), it is originally necessary to measure the concentration of the miscellaneous gas components. With this regard, the virtual basic-heating-value calculation unit 9 in the present invention calculates a value equivalent to the basic heating value by arithmetic operation, even when the concentration of the miscellaneous gas components is unknown. Specifically, on the basis of the heating value Hs of the target gas calculated by the heating value calculation unit 7 and the miscellaneous gas total approximate concentration y calculated by the miscellaneous gas total approximate-concentration calculation unit 8, the value corresponding to the basic heating value of the target gas when the miscellaneous gas components are assumed to be removed (i.e., the heating value of only the combustible gas component in the target gas) is obtained by arithmetic operation. In the present embodiment, the value equivalent to the basic heating value calculated by the virtual basic-heating-value calculation unit 9 is called the virtual basic heating value $H'_{HC}$. The output unit 20 outputs the virtual basic heating value $H'_{HC}$.

In general, measuring the concentration of the miscellaneous gas components is a large-scale and complicated task involving, for example, use of gas chromatography. In contrast, according to the calculation device 1 of the present embodiment, when the refractive index and the sound speed of the target gas (containing miscellaneous gas components) can be measured as inputs, the heating value (virtual basic heating value $H'_{HC}$) of only the combustible gas in the target gas can be calculated even in the case where the concentration of the miscellaneous gas components is unknown.

The virtual basic heating value $H'_{HC}$ output as a result of calculation by the calculation device 1 is used as a substitute of the basic heating value of the target gas. In other words, the virtual basic heating value $H'_{HC}$ can be used to calculate various physical property values (for example, a compression factor, a combustion speed, etc.) that can be calculated using the basic heating value. While the reason why such substitution is possible will be described in detail later, the refractive index measurement unit (refractive index calorimeter) and the sound speed measurement unit (sound speed sensor) are generally small and relatively inexpensive devices. Therefore, as compared to the conventional methods (calculation of the compression factor according to ISO12213-3 and calculation of the combustion speed by the (Pa) formula), the physical property values relating to the natural gas can be calculated simply and easily.

Figure 2A:
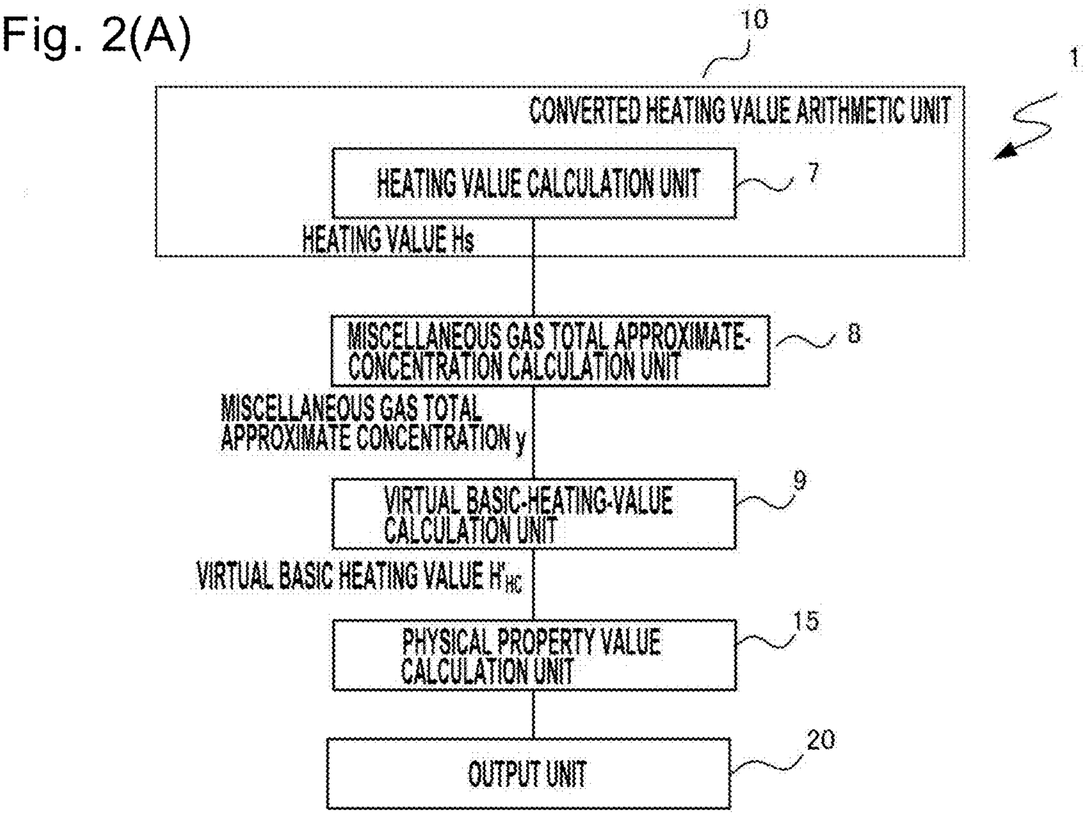
FIGS. 2(A)-2(C) are block diagrams showing an example of a calculation device according to the present embodiment.
Figure 2B:
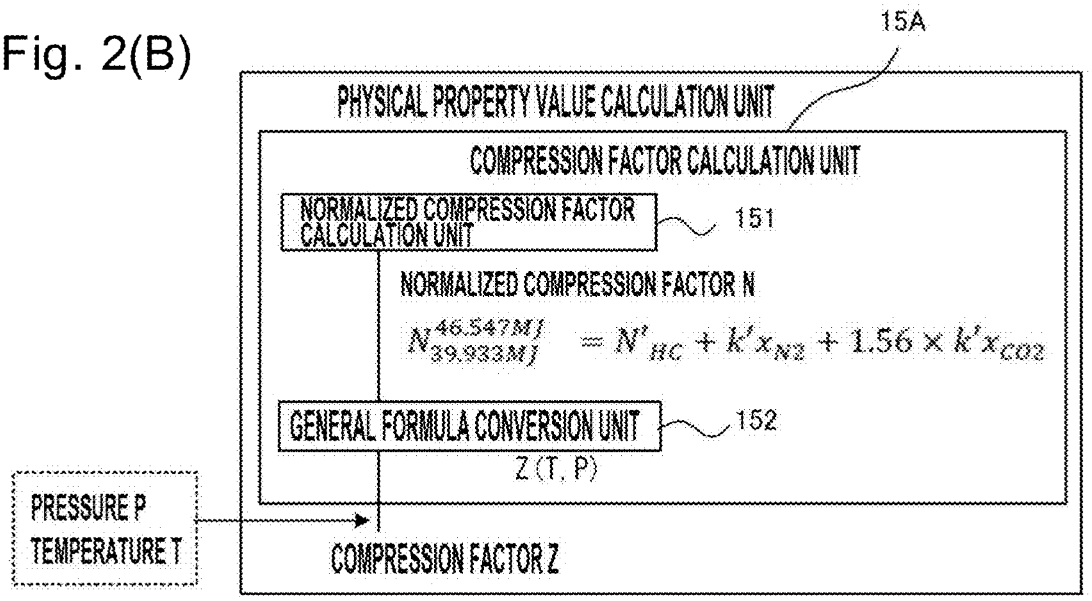
Figure 2C:
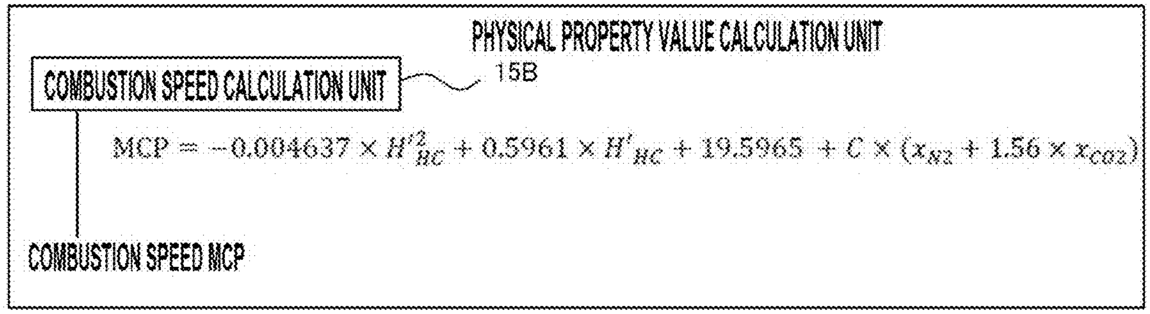

FIGS. 2(A)-(C) include schematic views showing an example of the calculation device 1 including a physical property value calculation unit 15 configured to calculate various physical property values relating to the target gas on the basis of the virtual basic heating value $H'_{HC}$. Component members identical to those shown in FIG. 1 are designated by identical reference signs to omit the description thereof. The component members other than the physical property value calculation unit 15 are similar to the component members in FIG. 1. FIG. 2(A) is a block diagram showing the overall configuration of the calculation device 1, and FIGS. 2(B) and 2(C) are block diagrams showing an example of the physical property value calculation unit 15.

FIG. 2(B) is an example of the case where the physical property value calculation unit 15 is a compression factor calculation unit 15A configured to calculate a compression factor. The compression factor calculation unit 15A includes a unit (normalized compression factor calculation unit) 151 configured to calculate a compression factor N that is normalized (hereinafter referred to as a "normalized compression factor"), and a general formula conversion unit 152 configured to convert the normalized compression factor N into a general formula.

Although described later in detail, the normalized compression factor N is a normalized expression of a gas compression factor, which is originally expressed as a function of the temperature T and the pressure P and is normalized so as to eliminate the influence of these parameters. The normalized compression factor calculation unit 151 has a normalized compression factor calculation formula (the formula (10) described later) and calculates the normalized compression factor N on the basis of the virtual basic heating value $H'_{HC}$ and the miscellaneous gas total approximate concentration y. The normalized compression factor calculation unit 151 corrects an error caused by using the miscellaneous gas total approximate concentration y and calculates the normalized compression factor N (this correction will be described later). The compression factor calculation unit 15A receives the input of the pressure P and the temperature T, generalizes the normalized compression factor N by the general formula conversion unit 152, and calculates a compression factor Z under the conditions of the pressure P and the temperature T to be required.

FIG. 2(C) is an example of the case where the physical property value calculation unit 15 is a combustion speed calculation unit 15B configured to calculates a combustion speed MCP. The combustion speed calculation unit 15B has a combustion speed calculation formula (the formula (15) described later) and calculates the combustion speed MCP on the basis of the virtual basic heating value $H'_{HC}$ and the miscellaneous gas total approximate concentration y. The combustion speed calculation unit 15B corrects an error caused by using the miscellaneous gas total approximate concentration y and calculates the combustion speed MCP (this correction will be described later).

Thus, the calculation device 1 of the present embodiment acquires two variables of the refractive index-converted heating value $H_{OPT}$ and the density-converted heating value $H_{SONIC}$, and uses the Opt-Sonic arithmetic operation to calculate the virtual basic heating value $H'_{HC}$. The calculation device 1 also approximately calculates a plurality of physical property values relating to a natural gas by using the virtual basic heating value $H'_{HC}$.

In the case where a physical property value is a value that can originally be calculated using the basic heating value of a natural gas in particular, the virtual basic heating value $H'_{HC}$ can be used as it is as a substitute of the basic heating value. For example, in a first method according to the method originally conceived by the applicant of the present invention as will be described later, the physical property values, such as the compression factor and the combustion speed, can be calculated by a polynomial formula (three input values (input parameters)) of three variables, i.e., the basic heating value of a natural gas, and the concentrations of a carbon dioxide gas and a nitrogen gas that are miscellaneous gas components. Therefore, the physical property values can be calculated more easily and with a configuration simpler compared with using the conventional calculation method according to ISO12213-3 or the (Pa) formula. In a second method, according to the present embodiment described above, the physical property values, such as the compression factor and the combustion speed, can be calculated with two input values, such as the refractive index and the density of the target gas, by using the virtual basic heating value as a substitute of the basic heating value. In other words, in calculation of the same physical property value, the second method can further reduce the number of input parameters as compared to the first method. In addition, the refractive index and the density of the target gas can be measured using small and relatively inexpensive devices, and therefore the plurality of physical property values relating to the natural gas, which can be calculated using the basic heating value $H_{HC}$, can be calculated simply and easily.

<Calculation Method and Program>

Figure 3A:
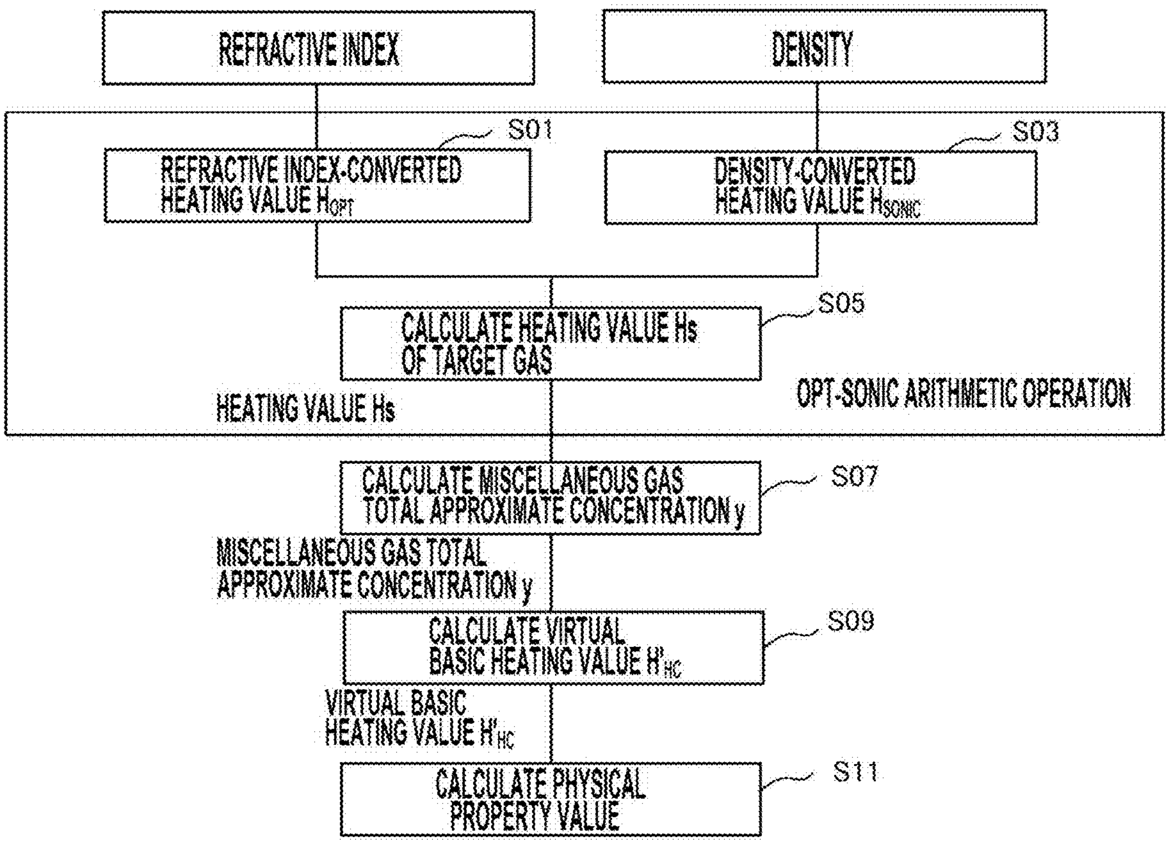
FIGS. 3(A)-3(C) include flowcharts showing an example of a calculation method according to the present embodiment.
Figure 3B:
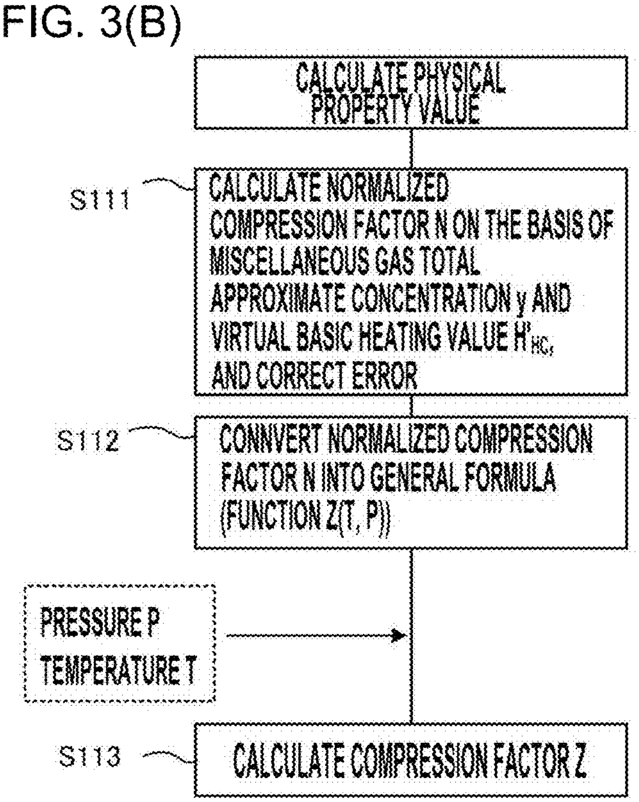
Figure 3C:
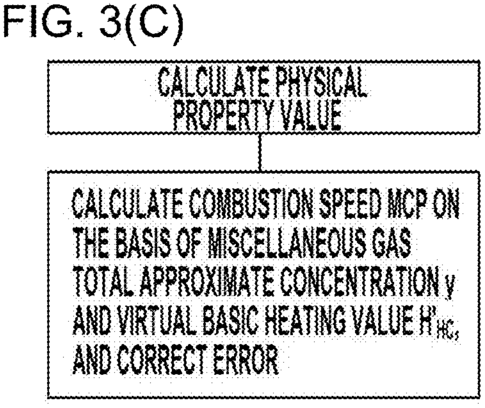

With reference to FIGS. 3(A)-(C), the embodiment of the present invention provides a method of calculating a physical property value relating to a combustible target gas containing miscellaneous gas components. Specifically, as shown in FIG. 3(A), the method relates to a calculation method, including: a step of measuring the refractive index of the target gas and acquiring the refractive index-converted heating value $H_{OPT}$(step S01); a step of measuring the density of the target gas and acquiring the density-converted heating value $H_{SONIC}$ (step S03); a step of calculating the heating value Hs of the target gas by the Opt-Sonic arithmetic operation on the basis of the refractive index-converted heating value $H_{OPT}$ and the density-converted heating value $H_{SONIC}$ (step S05); a step of calculating the approximate concentration of the miscellaneous gas components (a miscellaneous gas total approximate concentration y) by a miscellaneous gas total approximate concentration calculation formula on the basis of the refractive index-converted heating value $H_{OPT}$ and the density-converted heating value $H_{SONIC}$ (step S07); and a step of calculating the virtual basic heating value $H'_{HC}$ of the target gas by a virtual basic heating value calculation formula on the basis of the heating value Hs of the target gas and the miscellaneous gas total approximate concentration y (step S09). The calculated virtual basic heating value $H'_{HC}$ can be used, for example, to calculate various physical property values that can be acquired on the basis of the basic heating value $H_{HC}$ of the target gas (step S11).

As shown in FIG. 3(B), when the compression factor Z is calculated as an example of the physical property value, the normalized compression factor N is calculated on the basis of the miscellaneous gas total approximate concentration y calculated in step S07 in FIG. 3(A) and the virtual basic heating value $H'_{HC}$ calculated in step S09 in FIG. 3(A). In the calculation of the normalized compression factor N, an error caused by using the miscellaneous gas total approximate concentration y is corrected (error correction is performed) in accordance with miscellaneous gas components (a carbon dioxide gas concentration $x_{CO2}$) (step S111).

The normalized compression factor N is then converted into a general formula for the compression factor (function Z(T, P)) with the temperature T and the pressure P as parameters (step S112).

Then, given values to be input as the temperature T and the pressure P are input into the general formula (function Z(T, P)) to calculate the compression factor Z (step S113).

As shown in FIG. 3(C), when the combustion speed is calculated as an example of the physical property value, the combustion speed is calculated by a combustion speed calculation formula on the basis of the miscellaneous gas total approximate concentration y and the virtual basic heating value $H'_{HC}$. In the calculation of the combustion speed, an error caused by using the miscellaneous gas total approximate concentration y is corrected (error correction is performed).

The present embodiment of the present invention also provides a program for causing a computer to execute the above-described calculation method. The program is generally stored in a RAM or a ROM of the computer. Thus, the program is in the form of a non-transitory computer readable medium.

<Calculation Method of Physical Property Value that can Reduce Number of Input Parameters>

Next, as another embodiment of the present invention, a technique will be described that can reduce the number of input parameters in the calculation of the compression factor of a target gas and in the calculation method of the compression factor, as compared to the conventional methods (for example, the calculation method according to ISO12213-3 and the method according to the (Pa) formula). For example, when the target gas is a natural gas (paraffin-based hydrocarbon gas) that contains miscellaneous gas components mainly composed of a nitrogen gas and a carbon dioxide gas (that does not contain, or contains a negligible amount of, hydrogen and carbon monoxide), the compression factor and the combustion speed can be calculated by following methods.

<Calculation Method of Compression Factor>

Figure 4A:
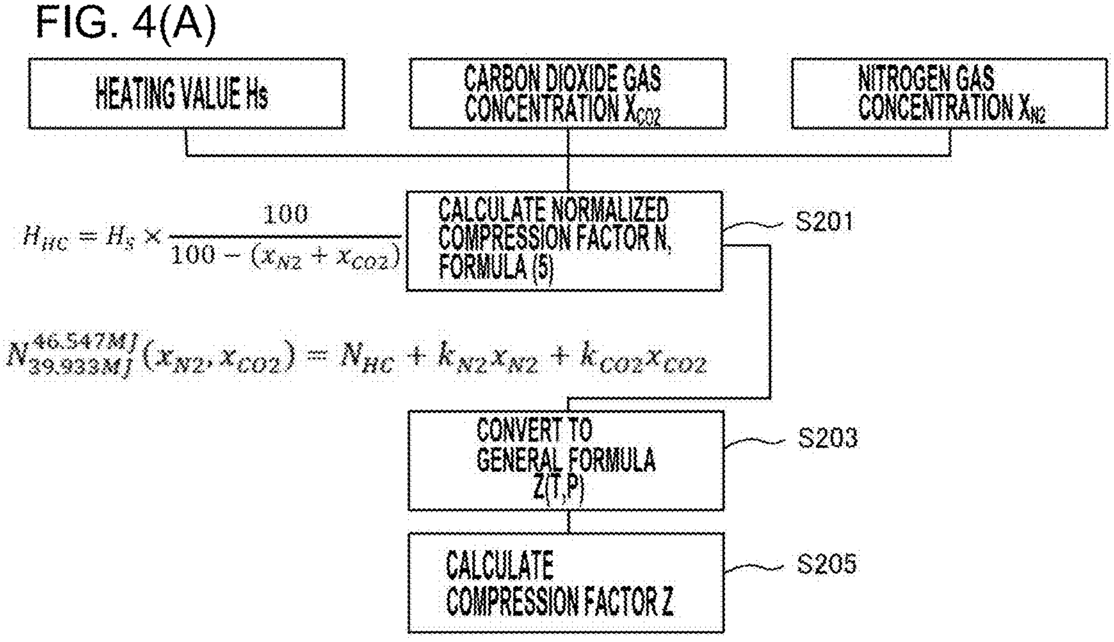
FIGS. 4(A) and 4(B) include flowcharts describing a calculation method of a compression factor in the present embodiment.
Figure 4B:
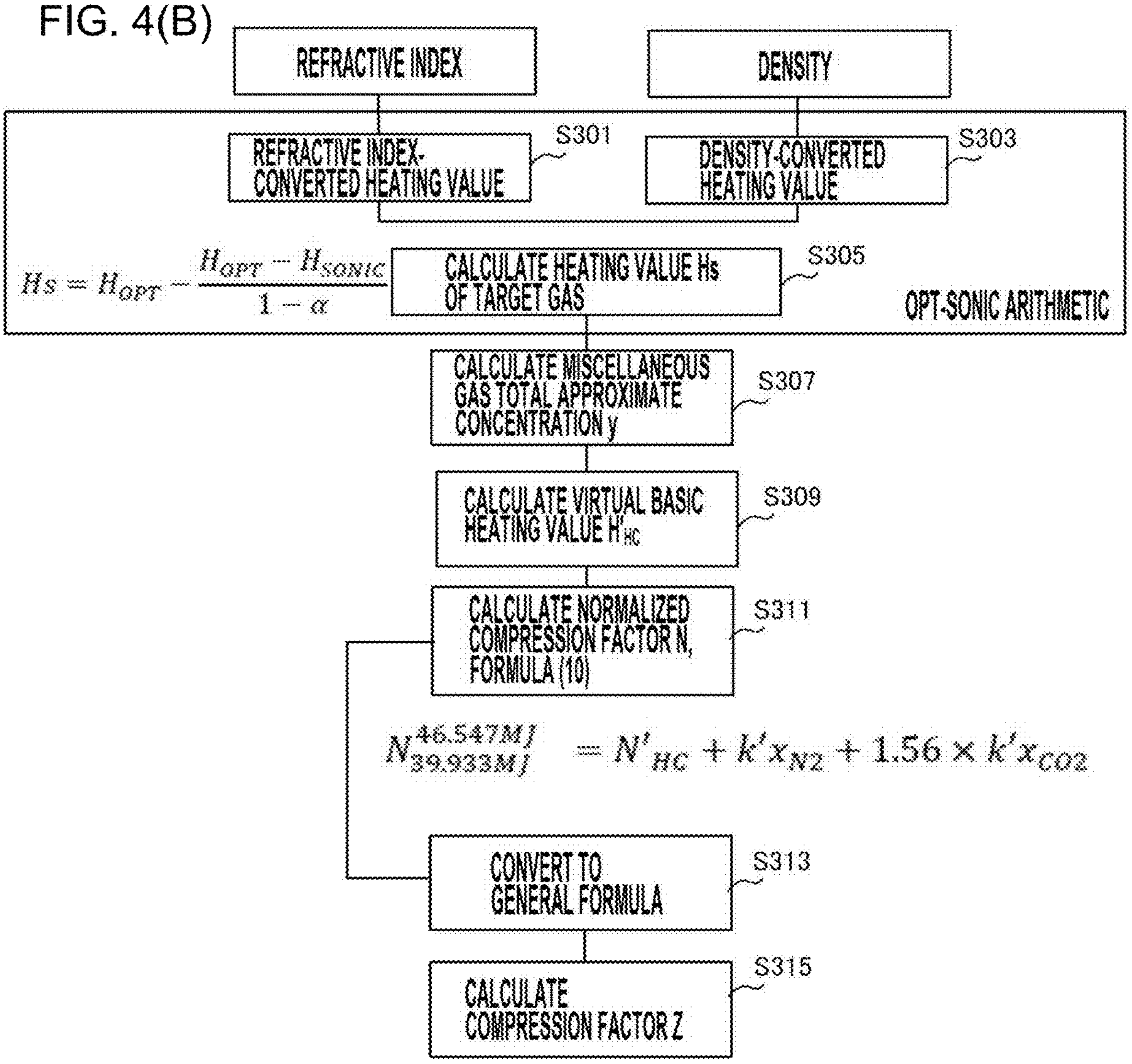

FIG. 4(A) is a flowchart showing a first method of calculating the compression factor Z. FIG. 4(B) is a flowchart showing a second method of calculating the compression factor Z.

(Compression Factor Calculation/First Method)

The first method is a method of calculating the compression factor Z using three input parameters, i.e., the heating value Hs of a natural gas, a carbon dioxide gas concentration $x_{CO2}$, and a nitrogen gas concentration $x_{N2}$. The method includes: a step of calculating the normalized compression factor N by inputting into a normalized compression factor calculation formula (the formula (5) described later) the heating value Hs of a natural gas, the carbon dioxide gas concentration $x_{CO2}$, and the nitrogen gas concentration $x_{N2}$ (step S201); a step of converting the normalized compression factor N into a general formula for the compression factor (function Z(T, P)) with the pressure P and the temperature T as parameters (step S203); and a step of calculating the compression factor Z under the conditions of the pressure P and the temperature T to be required (step S205).

The compression factor Z calculated using the calculation method according to ISO12213-3 is a value expressed as a function of a temperature T, a pressure P, a heating value Hs (a gross heating value converted to a measurement reference state temperature of 0° C., a combustion reference state of 25° C., and 101.325 kPa), a specific gravity d, and a carbon dioxide concentration $x_{CO2}$ (function Z(T, P, Hs, d, $x_{CO2}$)). The applicant of the present invention tried to normalize compression factors $Z_A$(T, P, Hs, d, $x_{CO2}$) and $Z_B$(T, P, Hs, d, $x_{CO2}$) of two different types of gases A and B so that their solutions are equal to 0 and −1, respectively. As a result, the applicant found that the compression factor Z can be expressed approximately by a polynomial formula of the basic heating value $H_{HC}$ based on the heating value Hs of a natural gas, the carbon dioxide gas concentration $x_{CO2}$, and the nitrogen gas concentration $x_{N2}$ (the formula (5) described later). The value obtained by the polynomial formula is the normalized compression factor N.

In the conventional technique (the calculation method according to ISO12213-3), the pressure P and the temperature T are used as initial input data. When the compression factor Z is calculated under the conditions of different temperatures and pressures, re-calculation must be performed starting from all the input data for the respective calculation methods, causing inconvenience.

According to the first method of compression factor calculation, three input parameters, the heating value Hs of a natural gas, and the carbon dioxide gas concentration $x_{CO2}$ and the nitrogen gas concentration $x_{N2}$ in the natural gas, are used to calculate the normalized compression factor N independent of the temperature T and the pressure P. In this case, the formulas (5) and (6) described later are used. The normalized compression factor N is further converted into a general formula (function Z(T, P)) with the temperature T and the pressure P as parameters. In other words, when the compression factor Z is calculated under the conditions of different temperatures and pressures, various compression factors Z can be calculated by changing only the input parameters, the temperature T and the pressure P in the general formula (function Z(T, P)).

Therefore, the first method of the compression factor calculation includes: calculating the basic heating value $H_{HC}$ on the basis of the heating value Hs of a natural gas, and the carbon dioxide gas concentration $x_{CO2}$ and the nitrogen gas concentration $x_{N2}$ in the natural gas; calculating the normalized compression factor N on the basis of the basic heating value $H_{HC}$, and the carbon dioxide gas concentration $x_{CO2}$ and the nitrogen gas concentration $x_{N2}$ in the natural gas; and calculating the compression factor Z on the basis of the normalized compression factor N.

(Compression Factor Calculation/Second Method)

With reference to FIG. 4(B), a second method of calculating the compression factor Z will be described. The second method is a method to further reduce the input parameters and calculate the compression factor Z on the basis of two input parameters, the refractive index and the density of a natural gas. Specifically, the second method includes: a step of calculating the refractive index-converted heating value $H_{OPT}$ on the basis of the refractive index (step S301); a step of calculating the density-converted heating value $H_{SONIC}$ on the basis of the density (step S303); a step of calculating the heating value Hs of a natural gas by the Opt-Sonic arithmetic formula on the basis of the refractive index-converted heating value $H_{OPT}$ and the density-converted heating value $H_{SONIC}$ (step S305); a step of calculating the miscellaneous gas total approximate concentration y (step S307); a step of calculating the virtual basic heating value $H'_{HC}$ (step S309); a step of calculating the normalized compression factor N (step S311); a step of converting the normalized compression factor N into a general formula for the compression factor (function Z(T, P)) with the temperature T and the pressure P as parameters (step S313); and a step of calculating the compression factor Z by inputting the pressure P and the temperature T required for the general formula (function Z (T, P)) (step S315).

The second method of the compression factor calculation corresponds to the calculation method for obtaining the compression factor Z as a physical property value described in FIGS. 3(A) and 3(B) above. According to the second method, the normalized compression factor N independent of the temperature T and the pressure P can be calculated with two input parameters, the refractive index and the density of a natural gas. In this case, the formula (10) described later is used. Then, the normalized compression factor N is converted into a general formula (function Z(T, P)) with the temperature T and the pressure P serving as parameters. In other words, when the compression factor Z is calculated under the conditions of different temperatures and pressures, various compression factors Z can be calculated by changing only the input parameters, the temperature T and the pressure P in the function Z(T, P)).

It is also possible to configure compression factor calculation devices capable of executing the above-described methods. Although illustration is omitted, a compression factor calculation device capable of executing the first method of compression factor calculation includes: an acquisition unit capable of acquiring each of the heating value Hs of a natural gas, the carbon dioxide gas concentration $x_{CO2}$, and the nitrogen gas concentration $x_{N2}$; a unit configured to calculate the basic heating value $H_{HC}$ on the basis of the heating value Hs, the carbon dioxide gas concentration $x_{CO2}$, and the nitrogen gas concentration $x_{N2}$; a normalized compression factor calculation unit that has a normalized compression factor calculation formula; a conversion unit for conversion to a general formula for the compression function (function Z(T, P)); and an output unit configured to output the calculated compression factor Z. It is also possible to configure a program for causing a computer to execute the above-described method.

A compression factor calculation device capable of executing the second method of compression factor calculation and a program are the same as the calculation device 1 described in FIGS. 2(A) and 2(B) described above, and so the description thereof is omitted.

<Calculation Method of Combustion Speed>

Figure 5A:
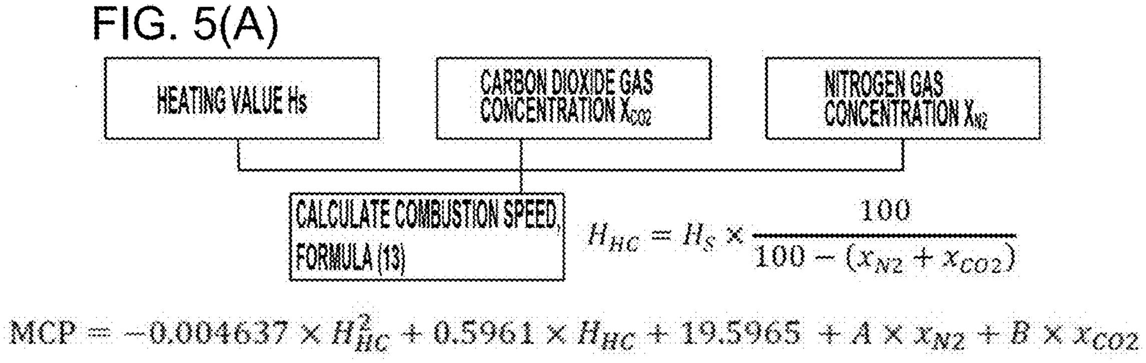
FIGS. 5(A) and 5(B) include flowcharts describing a calculation method of a combustion speed in the present embodiment.
Figure 5B:
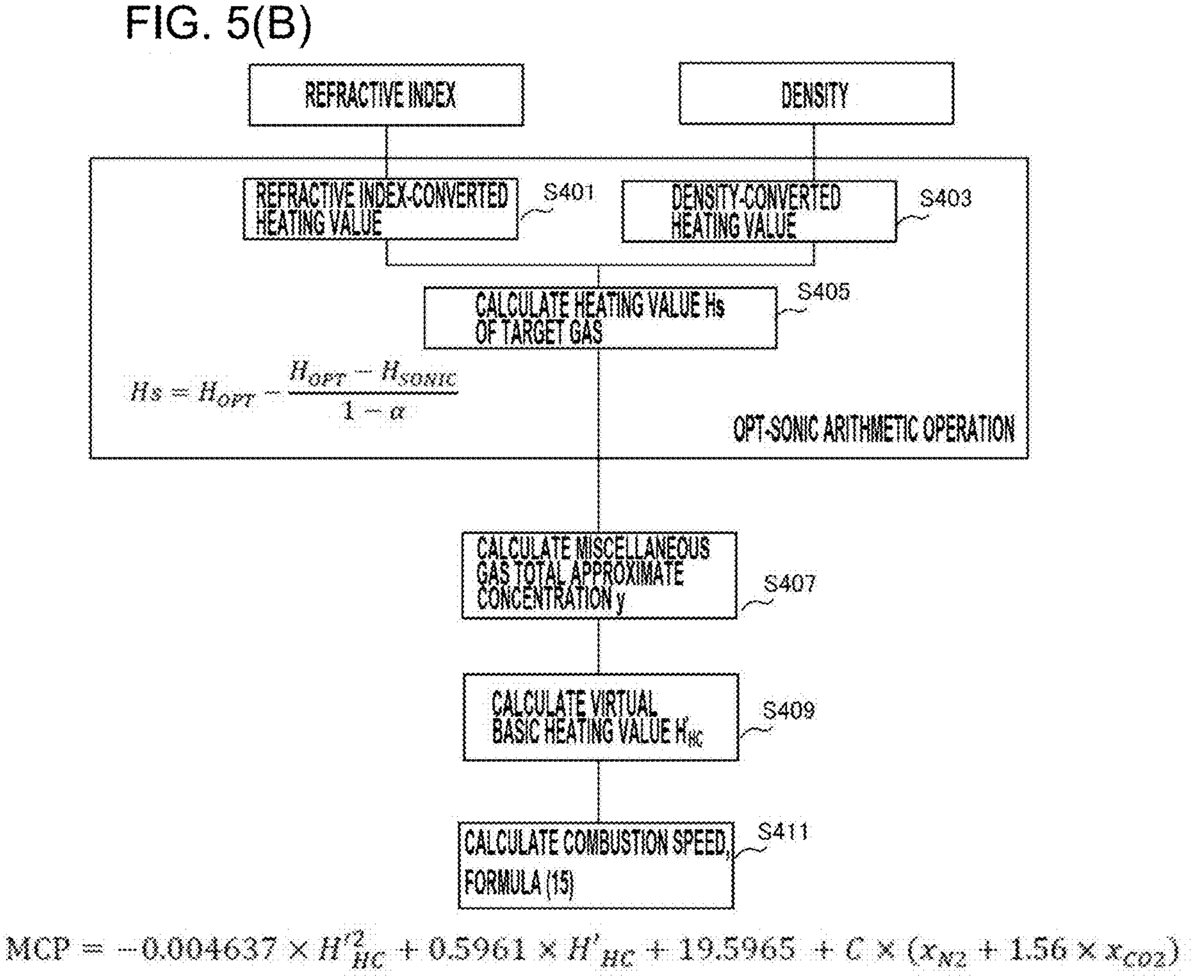

Next, with reference to FIGS. 5, a calculation method of the combustion speed will be described. FIG. 5(A) is a flowchart showing a first method of calculating the combustion speed. FIG. 5(B) is a flowchart showing a second method of calculating the combustion speed.

(Combustion Speed Calculation/First Method)

The first method of calculating the combustion speed is a method of calculating the combustion speed MCP using three input parameters, i.e., the heating value Hs of a natural gas, the carbon dioxide gas concentration $x_{CO2}$, and the nitrogen gas concentration $x_{N2}$ by using a combustion speed calculation formula shown in the formula (13) described later (and the formula (14)).

Specifically, the first method of calculating the combustion speed includes: calculating the basic heating value Hs on the basis of the heating value Hs of a natural gas, and the carbon dioxide gas concentration $x_{CO2}$ and the nitrogen gas concentration $x_{N2}$ in the natural gas; and calculating the combustion speed MCP on the basis of the basic heating value $H_{HC}$, and the carbon dioxide gas concentration $x_{CO2}$ and the nitrogen gas concentration $x_{N2}$ in the natural gas.

<Combustion Speed Calculation/Second Method>

With reference to FIG. 5(B), the second method of calculating the combustion speed MCP will be described. The second method is a method to further reduce the input parameters and calculate the combustion speed MCP on the basis of two input parameters, the refractive index and the density of a natural gas. Specifically, the second method includes: a step of calculating the refractive index-converted heating value $H_{OPT}$ on the basis of the refractive index (step S401); a step of calculating the density-converted heating value $H_{SONIC}$ on the basis of the density (step S403); a step of calculating the heating value Hs of a natural gas by the Opt-Sonic arithmetic formula on the basis of the refractive index-converted heating value $H_{OPT}$ and the density-converted heating value $H_{SONIC}$ (step S405); a step of calculating the miscellaneous gas total approximate concentration y (step S407); a step of calculating the virtual basic heating value $H'_{HC}$ (step S409); and a step of calculating the combustion speed MCP by a combustion speed calculation formula shown in the formula (15) described later (step S411).

The second method corresponds to the calculation method of obtaining the combustion speed as a physical property value described in FIGS. 3(A) and 3(C) above. According to the second method, the combustion speed MCP can be calculated using two input parameters, the refractive index and the density of a natural gas.

It is also possible to configure combustion speed calculation devices capable of executing the above-described methods. Although illustration is omitted, a combustion speed calculation device capable of executing the first method of calculating the combustion speed includes: an acquisition unit capable of acquiring each of the heating value Hs of a natural gas, the carbon dioxide gas concentration $x_{CO2}$, and the nitrogen gas concentration $x_{N2}$; a unit configured to calculate the basic heating value $H_{HC}$ on the basis of the heating value Hs, the carbon dioxide gas concentration $x_{CO2}$, and the nitrogen gas concentration $x_{N2}$; a combustion speed calculation unit having a combustion speed calculation formula; and an output unit configured to output the calculated combustion speed MCP. It is also possible to configure a program for causing a computer to execute the above-described method.

A combustion speed calculation device capable of executing the second method of calculating the combustion speed and a program are the same as the calculation device 1 described in FIGS. 2(A) and 2(C) above, and so the description thereof is omitted.

A detailed description will now be given of simulations and consideration on the basis of which the applicant of the present invention could conceive the configuration of the respective embodiments, and the calculation formulas (functions) derived on the basis of these simulations and consideration.

<Normalized Compression Factor N>

A description will be given of the concept of the normalized compression factor N and the calculation method thereof as conceived by the applicant of the present invention. A natural gas in the following description is a gas having a paraffin-based hydrocarbon gas as a main component.

First, the calculation method of the compression factor Z according to ISO12213-3 was used to examine the characteristics of a compression factor $Z_{HC}$ of a natural gas composed only of paraffin-based hydrocarbon gases having $CH_4$ as a main component. In this case, the compression factor $Z_{HC}(P,T)$ under the conditions of the pressure P and the temperature T changes depending on a heating value $H_{HC}$ regardless of its composition. In other words, as shown in the formula (1) shown below, the compression factor $Z_{HC}(P,T)$ can be expressed as a polynomial formula (a function determined by the pressure P and the temperature T) of the heating value (i.e., the basic heating value in the following explanation) $H_{HC}$.

[Mathematical formula 1]

$$Z_{HC}(P, T) = \sum_{h=0}^{3} a_h(P, T) H_{HC}^h \qquad (1)$$

Here, $a_h$ (a3, a2, a1, a0) in the formula (1) represent coefficients of respective polynomial terms.

Figure 6:
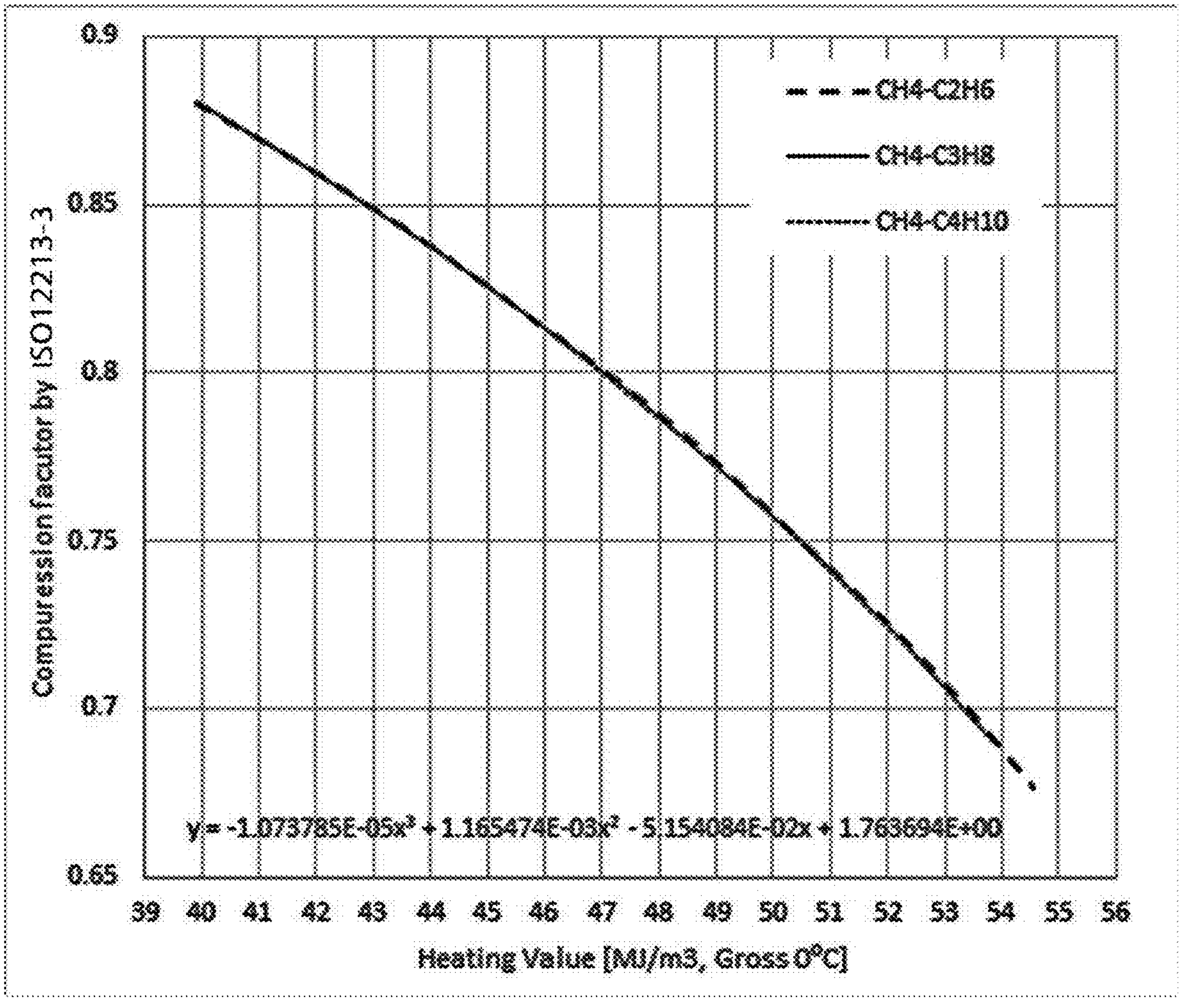
FIG. 6 is a graph showing an example of the relation between the heating value and the compression factor of gases.

FIG. 6 is a graph showing an example of the relation between the heating value $H_{HC}$ and the compression factor $Z_{HC}$ of gases expressed by the formula (1). The horizontal axis represents the heating value $H_{HC}$ of the gases composed only of paraffin-based hydrocarbon gases, and the vertical axis represents the compression factor $Z_{HC}$ under the conditions of a pressure of 7 MPa and a temperature of 20° C.

Here, as the paraffin-based hydrocarbon gases, three types of mixed gases, containing methane ($CH_4$), ethane ($C_2H_6$), propane ($C_3H_8$), and butane ($C_4H_{10}$) in different proportions, were used. The heating values $H_{HC}$ of the respective gases under the conditions of a pressure of 7 MPa and a temperature of 20° C. were calculated by the calculation according to ISO6976. The compression factors $Z_{HC}$ of the respective gases under the conditions of a pressure of 7 MPa and a temperature of 20° C. were also calculated by the calculation method according to ISO12213-3. As a result, in all the cases, the correlation between the heating value $H_{HC}$ and the compression factor $Z_{HC}$ approximately coincide (respective curves indicating the relations of the three types of gases for the most part overlap in FIG. 6). Therefore, these correlations can be expressed by a polynomial formula of the heating value $H_{HC}$, as shown in the formula (2) below.

[Mathematical formula 2]

$$Z_{HC}(7MPa, 20^\circ\ C.) = -1.073785 \times 10^{-5} H_{HC}^3 + 0.001165474 H_{HC}^2 - 0.05154084 \times H_{HC} + 1.763694 \qquad (2)$$

Here, the applicant of the present invention examined the relation between the heating value $H_{HC}$ and the compression factor $Z_{HC}$ as a relation independent of the pressure P and the temperature T. Then, for two types of gases A and B, which had the correlation shown in FIG. 6 and which were different in heating value (for example, the heating value of gas A<the heating value of gas B), normalization of the compression factor was performed using the formula (3) so that a solution to a compression factor $Z_A$(T,P) of the gas A and a solution to a compression factor $Z_B$(T,P) of the gas B were equal to 0 and −1, respectively.

[Mathematical formula 3]

$$N_A^B = -\frac{Z_{HC}(T,P) - Z_A(T,P)}{Z_B(T,P) - Z_A(T,P)} \tag{3}$$

As an example, assuming that the gas A was a gas with a heating value $H_{HC}$ of 39.933 MJ/m$^3$ (pure methane, a gas of $CH_4$=100%) and the gas B was a gas with a heating value of 46.547 MJ/m$^3$ (a gas having a composition of $CH_4$:$C_2H_6$:$C_3H_8$:$C_4H_{10}$=86:8:4:2), the compression factors of the respective gases were normalized using the formula (3) so that the solution to a compression factor $Z_{390.933\ MJ}$ (T, P) of the gas A and the solution to a compression factor $Z_{46.547\ MJ}$ (T, P) of the gas B were equal to 0 and −1, respectively.

As a result, it was found that the normalized value (N) can be expressed approximately by the function of only the heating value $H_{HC}$ as shown in the following formula (4-1).

[Mathematical formula 4]

$$N_{39.933MJ}^{46.547MJ} = -\frac{Z_{HC}(T,P) - Z_{39.933MJ}(T,P)}{Z_{46.547MJ}(T,P) - Z_{39.933MJ}(T,P)} \tag{4}$$

$$\approx -0.000144197 \times H_{HC}^3 + 0.0156245 \times H_{HC}^2 - 0.690859 \times H_{HC} + 11.8568 \tag{4-1}$$

Thus, when a natural gas was composed only of paraffin-based hydrocarbon gases, it was possible to express the result (N) of normalizing the compression factor Z, as a polynomial formula of the heating value $H_{HC}$ independent of the pressure P and the temperature T. The result (N) is hereinafter referred to as the "normalized compression factor N". The normalized compression factor N in the formula has suffixes corresponding to the respective heating values of the gas A and the gas B (an upper suffix: 46.547 MJ, and a lower suffix: 39.933 MJ) (N^{46.547 MJ}_{39.933 MJ}). In the following descriptions, these suffixes are omitted, and the normalized compression factor is simply expressed as "N".

Figure 7A:
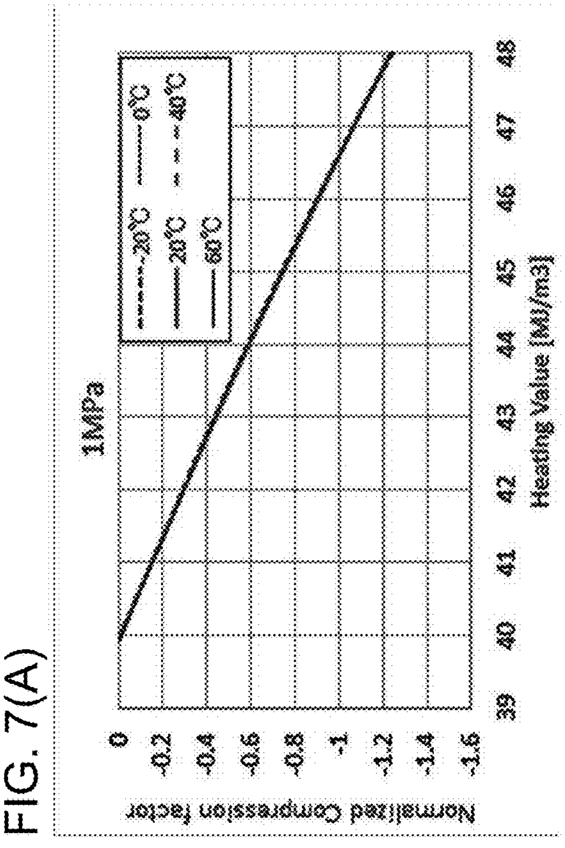
FIGS. 7(A)-7(D) show the results of verification of normalized compression factors calculated by the present embodiment.
Figure 7B:
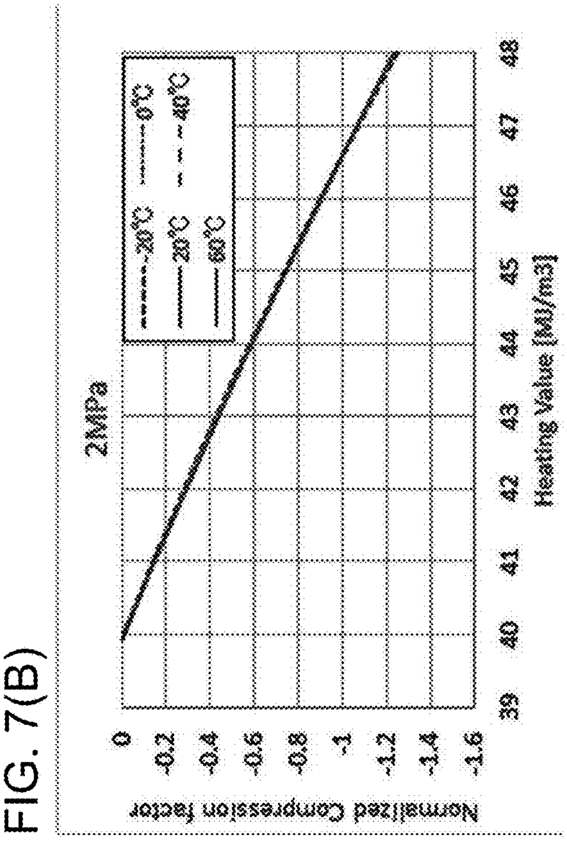
Figure 7C:
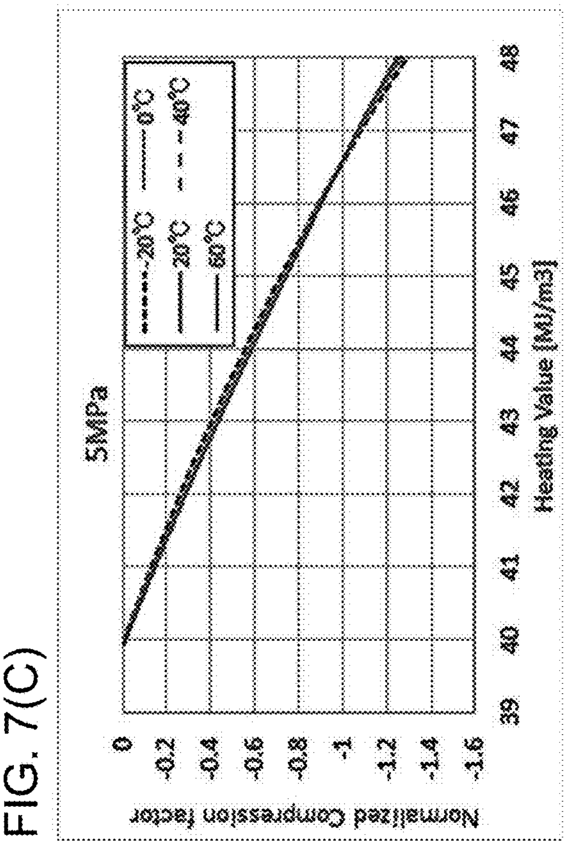
Figure 7D:
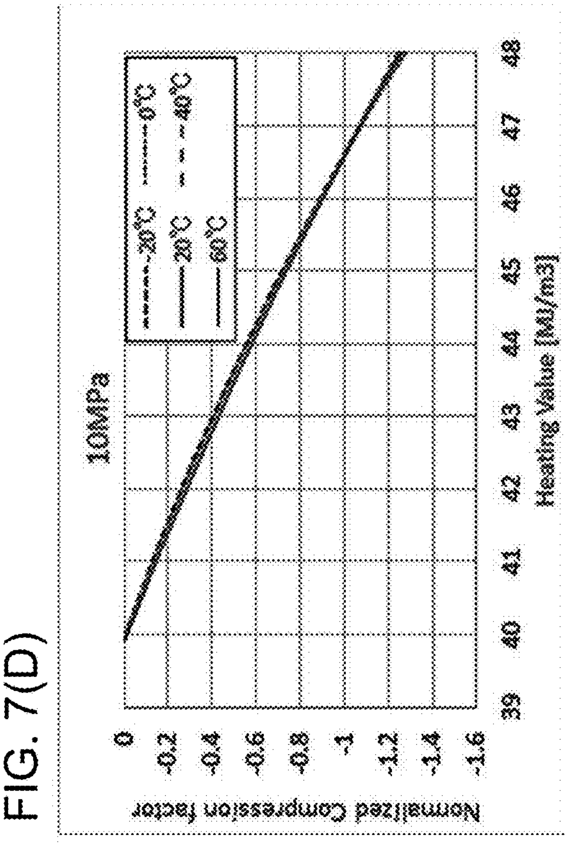

FIGS. 7(A)-7(D) show the results of verification of the normalized compression factors N calculated by the formula (4), in the form of graphs indicating the relation between a measured value of the heating value $H_{HC}$ and the normalized compression factor N under conditions of different pressures P and temperatures T. Herein, FIG. 7(A) shows the case of the pressure being 1 MPa, FIG. 7(B) shows the case of the pressure being 2 Mpa, FIG. 7(C) shows the case of the pressure being 5 Mpa, and FIG. 7(D) shows the case of the pressure being 10 Mpa. In each case, the heating values $H_{HC}$ of the natural gas (gas composed only of paraffin-based hydrocarbon gases) under the conditions of temperatures of −20° C., 0° C., 20° C., 40° C., and 60° C. were obtained by calculations according to ISO6976. The normalized compression factors N under the above-described conditions were also calculated using the formula (4). The horizontal axis represents the heating value $H_{HC}$, and the vertical axis represents the normalized compression factor N. It was found out that curves indicating the correlation between the heating value $H_{HC}$ and the normalized compression factor N can be expressed for the most part by a single curve even when the pressure P and the temperature T varies between any of the conditions shown in FIG. 7. On the basis of this result, it was also found that when a natural gas is composed only of paraffin-based hydrocarbon gases, the normalized compression factor N can be expressed approximately by the polynomial formula (4-1) of the heating value $H_{HC}$.

Next, examination was made regarding the influence of the gas, composed only of paraffin-based hydrocarbon gases having the heating value $H_{HC}$ and the normalized compression factor $N_{HC}$, on the normalized compression factor $N_{HC}$, when a nitrogen gas $x_{N2}$ [mol %] and a carbon dioxide gas $x_{CO2}$ [mol %] were added.

As a result, it was found that the normalized compression factor N($x_{N2}$, $x_{CO2}$) of a natural gas, when a nitrogen gas $x_{N2}$ [mol %] and a carbon dioxide gas $x_{CO2}$ [mol %] are added, can also be expressed approximately by the function of the heating values $H_{HC}$ of paraffin-based hydrocarbon gas components, without receiving significant influence of the pressure P and the temperature T, as shown by the formula (5) below.

[Mathematical formula 5]

$$N_{39.933MJ}^{46.547MJ}(x_{N2}, x_{CO2}) = N_{HC} + k_{N2}x_{N2} + k_{CO2}x_{CO2} \tag{5}$$

provided that $$N_{HC} = -0.000144197 \times H_{HC}^3 + 0.0156245 \times H_{HC}^2 - 0.690859 \times H_{HC} + 11.8568 \tag{5.1}$$

$$k_{N2} = a_{N2} \times H_{HC}^2 - b_{N2} \times H_{HC} + c_{N2},\ \text{here } a_{N2} = 0.000139157,\ b_{N2} = 0.00972504,\ c_{N2} = 0.189587 \tag{5.2}$$

$$k_{CO2} = 0.0000535291 \times H_{HC}^2 - 0.00414912 \times H_{HC} + 0.0588733 \tag{5.3}$$

A coefficient $k_{N2}$ is a coefficient ($N_2$ correction coefficient) that corrects a change caused by a nitrogen gas contained as miscellaneous gas components in a natural gas (influence of a nitrogen gas as miscellaneous gas), and $k_{CO2}$ is a coefficient ($CO_2$ correction coefficient) that corrects a change caused by a carbon dioxide gas contained as miscellaneous gas components in a natural gas (influence of a carbon dioxide gas as a miscellaneous gas). The coefficients $k_{N2}$ and $k_{CO2}$ can also be expressed approximately by a polynomial formula of the heating value $H_{HC}$ of the paraffin-based hydrocarbon gas components in a natural gas.

As repeatedly stated, the heating value $H_{HC}$ described so far represents the heating value when a natural gas is composed only of paraffin-based hydrocarbon gases or represents the heating value of only the paraffin-based hydrocarbon gas components in a natural gas (i.e., the basic heating value $H_{HC}$ of the natural gas) excluding the miscellaneous gas components when the natural gas contains miscellaneous gases (a nitrogen gas and a carbon dioxide gas).

Here, when a natural gas contains a nitrogen gas (a nitrogen gas concentration $x_{N2}$ [mol %]) and a carbon dioxide gas (a carbon dioxide gas concentration $x_{CO2}$ [mol %]) as miscellaneous gas components, the relation between the gross heating value Hs and the basic heating value $H_{HC}$ of the natural gas is expressed by the formula (6) below.

[Mathematical formula 6]

$$H_{HC} = H_S \times \frac{100}{100-(x_{N2}+x_{CO2})} \quad (6)$$

Specifically, by the formula (6), the formula (5) functions as the formula (normalized compression factor calculation formula) that calculates the normalized compression factor N, which is constituted of three input parameters, i.e., the heating value Hs of a natural gas, the carbon dioxide gas concentration $x_{CO2}$, and the nitrogen gas concentration $x_{N2}$ and which is not influenced by the pressure P or the temperature T. Therefore, as for the natural gas containing miscellaneous gas components, it can be said that when the heating value (gross heating value) Hs of the natural gas, the carbon dioxide gas concentration $x_{CO2}$, and the nitrogen gas concentration $x_{N2}$ can be acquired, the basic heating value $H_{HC}$ can be calculated by the formula (6), and the normalized compression factor N of the natural gas can be calculated by the formula (5).

On the basis of this consideration, in the normalized compression factor calculation method described with reference to FIG. 4(A) described above, the normalized compression factor N is calculated with three elements, i.e., the heating value (gross heating value) Hs of a target gas (a natural gas), the carbon dioxide gas concentration $x_{CO2}$, and the nitrogen gas concentration $x_{N2}$ as input parameters, using the above-described formula (5) (and the formula (6)) as the normalized compression factor calculation formula. By introducing the concept of the normalized compression factor N, the compression factor can be calculated by converting the normalized compression factor N into a general formula for calculation of the compression factor Z and then by optionally changing only the parameters, the pressure P and the temperature T.

<Calculation Method of Compression Factor Using Opt-Sonic Arithmetic Operation>

In the normalized compression factor calculation method shown in FIG. 4(A), the carbon dioxide gas concentration $x_{CO2}$ and the nitrogen gas concentration $x_{N2}$, which are miscellaneous gas components, (i.e., the measurements of these) are essential as input parameters. The applicant of the present invention further examined the method of calculating the compression factor Z using the Opt-Sonic arithmetic operation without measuring the individual concentrations of miscellaneous gas components.

As described before, the Opt-Sonic arithmetic operation can calculate the heating value Hs on the basis of, for example, the refractive index-converted heating value $H_{OPT}$ obtained from a refractive index of a target gas measured by an optical sensor or the like and on the basis of, for example, the density-converted heating value $H_{SONIC}$ obtained from a density of a target gas measured by a sound speed sensor or the like, and by using an arithmetic formula of a converted heating value (Opt-Sonic arithmetic formula) shown by the formula (7) below. In other words, the arithmetic formula of a converted heating value (Opt-Sonic arithmetic formula) described with reference to FIGS. 1 to 5 described above is expressed by the formula (7) below.

[Mathematical formula 7]

$$Hs = H_{OPT} - \frac{H_{OPT}-H_{SONIC}}{1-\alpha} \quad (7)$$

Here, a second term of the right side of the formula (7) indicates the value of an error component, due to miscellaneous gas contained in the natural gas, included in the refractive index-converted heating value $H_{OPT}$. The value corresponds to the "error correction value" in the description with reference to FIGS. 1 to 5 described above. A variable "a" in a second term of the right side is a correction coefficient that may be substantially constant regardless of the types of miscellaneous gases when considered within a certain range of values (a range of certain gas types). As an example, the value of the correction coefficient α is in the range of α=1.5 to 3.5.

As a result of the consideration by the applicant of the present invention, it was found that when the miscellaneous gas in the natural gas can be regarded as being composed only of a nitrogen gas and a carbon dioxide gas, a second term of the right side is proportional to the sum of the value of the nitrogen gas concentration $x_{N2}$ and the value of the carbon dioxide gas concentration $x_{CO2}$ multiplied by 1.56 as shown in the formula (8) below. Note that even if components other than a nitrogen gas and a carbon dioxide gas (for example, a hydrogen gas, a carbon monoxide gas, etc.) are contained as miscellaneous gas components, the proportional content of components other than a nitrogen gas and a carbon dioxide gas in a natural gas is very small, and there seems to be no influence on the calculation values in this consideration (this also applies to the following).

[Mathematical formula 8]

$$\frac{1}{0.2529} \times \frac{H_{OPT}-H_{SONIC}}{1-\alpha} = (x_{N2}+1.56 \times x_{CO2}) = y \quad (8)$$

Accordingly, by regarding the result of the formula (8) as a variable y, and manipulating the variable y and assigning it to the right side of the formula (6), a value corresponding to the basic heating value $H_{HC}$ in the formula (6) can be calculated (the formula (9) below). The variable y is a total approximate concentration of a nitrogen gas and a carbon dioxide gas, i.e., the "miscellaneous gas total approximate concentration y" in the descriptions referring to FIGS. 1 to 5 described above, and the formula (8) is a miscellaneous gas total approximate concentration calculation formula. As shown by the formula (8), the "miscellaneous gas total approximate concentration y" can be calculated from the Opt-Sonic arithmetic operation. In other words, even when the respective concentrations of miscellaneous gas components (the nitrogen gas concentration $x_{N2}$ and the carbon dioxide gas concentration $x_{CO2}$) are unknown (that is, without measuring the concentrations of the miscellaneous gas components), the miscellaneous gas total approximate concentration y can be calculated on the basis of the refractive index-converted heating value $H_{OPT}$ and the density-converted heating value $H_{SONIC}$. For the formula (6), when the carbon dioxide gas concentration $x_{CO2}$ that is approximated to be 1.56 times the actual value is used instead of the carbon dioxide gas concentration $x_{CO2}$, and the nitrogen gas concentration $x_{N2}$ and the carbon dioxide gas concentration $x_{CO2}$ are forcibly replaced with the miscellaneous gas total approximate concentration y by allowing an approximation error, the following formula (9) is obtained.

[Mathematical formula 9]

$$H'_{HC} = Hs \times \frac{100}{100-y} = Hs \times \frac{100}{100-(x_{N2}+1.56 \times x_{CO2})} \quad (9)$$

As a result, for the formula (9), the variable Hs can be calculated from the Opt-Sonic arithmetic operation in the formula (7), and the variable y can be calculated from the Opt-Sonic arithmetic operation in the formula (8). Therefore, the formula (9) is a formula that uses the Opt-Sonic arithmetic operation to virtually calculate the basic heating value (the virtual basic heating value $H'_{HC}$). The formula (9) is the "virtual basic heating value calculation formula" in the descriptions referring to FIGS. 1 to 5 described above. The virtual basic heating value $H'_{HC}$ can be used as a substitute value (approximate value) for the basic heating value $H_{HC}$ of a natural gas obtained by measuring the respective concentrations of miscellaneous gas components and performing calculation by the formula (6).

Then, in the calculation formula of the normalized compression factor N by the formula (5), when the basic heating value $H_{HC}$ is replaced with the virtual basic heating value $H'_{HC}$ of the above-described formula (9) with minor modifications, the formula (10) below can be acquired. Therefore, the formula (10) is also a normalized compression factor calculation formula similar to the formula (5). As described before, since the virtual basic heating value $H'_{HC}$ can be calculated using the Opt-Sonic arithmetic operation, the normalized compression factor of the formula (10) can be calculated even when the concentrations of miscellaneous gas components (the nitrogen gas concentration $x_{N2}$ and the carbon dioxide gas concentration $x_{CO2}$) are unknown.

[Mathematical formula 10]

$$N_{39.933MJ}^{46.547MJ} = N'_{HC} + k' \times y = N'_{HC} + k' x_{N2} + 1.56 \times k' x_{CO2} \qquad (10)$$

provided that $$N'_{HC} = -0.000144197 \times H'^{3}_{HC} + 0.0156245 \times H'^{2}_{HC} - 0.690859 \times H'_{HC} + 11.8568 \qquad (10.1)$$

$$k' = 0.85 \times a_{N2} \times H'^{2}_{HC} - 0.85 \times b_{N2} \times H'_{HC} + 0.85 \times c_{N2}, \text{ here} \qquad (10.2)$$

$$a_{N2} = 0.000139157,\ b_{N2} = 0.00972504,\ c_{N2} = 0.189587$$

In the formulas (10) and (10.1), $N'_{HC}$ is a virtual normalized compression factor of the natural gas that does not include (excludes) the miscellaneous gas components and that corresponds to the virtual basic heating value $H'_{HC}$ of the natural gas not including (excluding) the miscellaneous gas components. In other words, $N'_{HC}$ is an arithmetic normalized compression factor, that is, a virtual normalized compression factor that assumes that a natural gas is composed only of paraffin-based hydrocarbon (without including miscellaneous gases) and that the basic heating value is a virtual basic heating value H.

In the formula (10), k' is a coefficient to correct a change in the virtual normalized compression factor, which corresponds to the virtual basic heating value $H'_{HC}$. This change is due to the natural gas containing a nitrogen gas and a carbon dioxide gas as miscellaneous gas components (an overall influence of the nitrogen gas and the carbon dioxide gas as miscellaneous gases). Hereinafter, k' is referred to as a "miscellaneous gas correction coefficient".

The formula (10.1) is the same in terms of coefficients to the formula (5.1), while the basic heating value $H_{HC}$ in the formula (5.1) is replaced with the virtual basic heating value $H'_{HC}$.

The formula (10.2) is a formula to select and calculate the miscellaneous gas correction coefficient (k'), this calculation being made with reference to the $N_2$ correction coefficient $k_{N2}$ of the formula (5.2). Specifically, in order to "correct the overall influence of a nitrogen gas and a carbon dioxide gas as miscellaneous gases", a coefficient ($N_2$ correction coefficient $k_{N2}$) that "corrects the influence of the nitrogen gas as a miscellaneous gas" is used. As the basic heating value, the virtual basic heating value $H'_{HC}$ is used. Specifically, the basic heating value $H_{HC}$ of the right side of the formula (5.2) is replaced with the virtual basic heating value $H'_{HC}$, and coefficients $a_{N2}$, $b_{N2}$, and $c_{N2}$ in respective terms of the right side of the formula (5.2) are multiplied by a prescribed constant (0.85 in this case) to calculate the miscellaneous gas correction coefficient k'. The prescribed constant (0.85) in this case is a value that can be set (adjusted) on the basis of the type (the concentration of a carbon dioxide gas that is assumed to be contained in the target gas as a miscellaneous gas) of a target gas (a natural gas). The prescribed constant is hereinafter referred to as an "adjustment coefficient D". The adjustment coefficient D will be described later in detail.

Therefore, in the formula (10), as a change (amount) due to the presence of miscellaneous gas components, the miscellaneous gas total approximate concentration y is used instead of the values (measured values) of the nitrogen gas concentration $x_{N2}$ and the carbon dioxide gas concentration $x_{CO2}$. A change (deviation) caused by using the miscellaneous gas total approximate concentration y is corrected by the miscellaneous gas correction coefficient k' calculated on the basis of the $N_2$ correction coefficient $k_{N2}$.

Thus, according to the formula (10), the normalized compression factor N, which is not influenced by the pressure P or the temperature T, can be calculated on the basis of two parameters, the refractive index (refractive index-converted heating value $H_{OPT}$) and the density (density-converted heating value $H_{SONIC}$) of a natural gas.

On the basis of this consideration, in the normalized compression factor calculation method described with reference to FIG. 4(B) described above, two elements of the refractive index and the density of a natural gas are used as input parameters, and the above-described formula (10) is used as the normalized compression factor calculation formula to calculate the normalized compression factor N. By introducing the concept of the normalized compression factor N, the compression factor can be calculated by converting the normalized compression factor into a general formula for calculation of the compression factor and then by optionally changing only the parameters, the pressure P and the temperature T. In addition, the number of the input parameters can be reduced as compared to the normalized compression factor calculation method using the formula (5).

These findings are based on the fact that the normalized compression factor N by the formula (5) and the normalized compression factor N by the formula (10) produce substantially equal values for the same type of natural gases under the same conditions (pressure, temperature, etc.). This will be described below.

In the formula (5), a normalized compression factor $N_{HC}$ is calculated on the basis of the basic heating value $H_{HC}$ of a natural gas, and the correction terms corresponding to individually measured nitrogen gas concentration $x_{N2}$ and carbon dioxide gas concentration $x_{CO2}$ are added to the normalized compression factor $N_{HC}$ to correct an error due to the miscellaneous gas components, so as to calculate the normalized compression factor $N(x_{N2}, x_{CO2})$ in consideration of the miscellaneous gas components. Specifically, the nitrogen gas concentration $x_{N2}$ is multiplied by the $N_2$ correction coefficient $k_{N2}$, the carbon dioxide gas concentration $x_{CO2}$ is multiplied by the $CO_2$ correction coefficient $k_{CO2}$, and these correction terms are added.

Meanwhile, in the formula (10), the correction term of multiplying the miscellaneous gas total approximate concentration y by the miscellaneous gas correction coefficient k' is added to the arithmetic normalized compression factor, that is, a virtual normalized compression factor $N'_{HC}$ to correct an error due to the miscellaneous gas components, so as to calculate the normalized compression factor N in consideration of the miscellaneous gas components.

Figure 8:
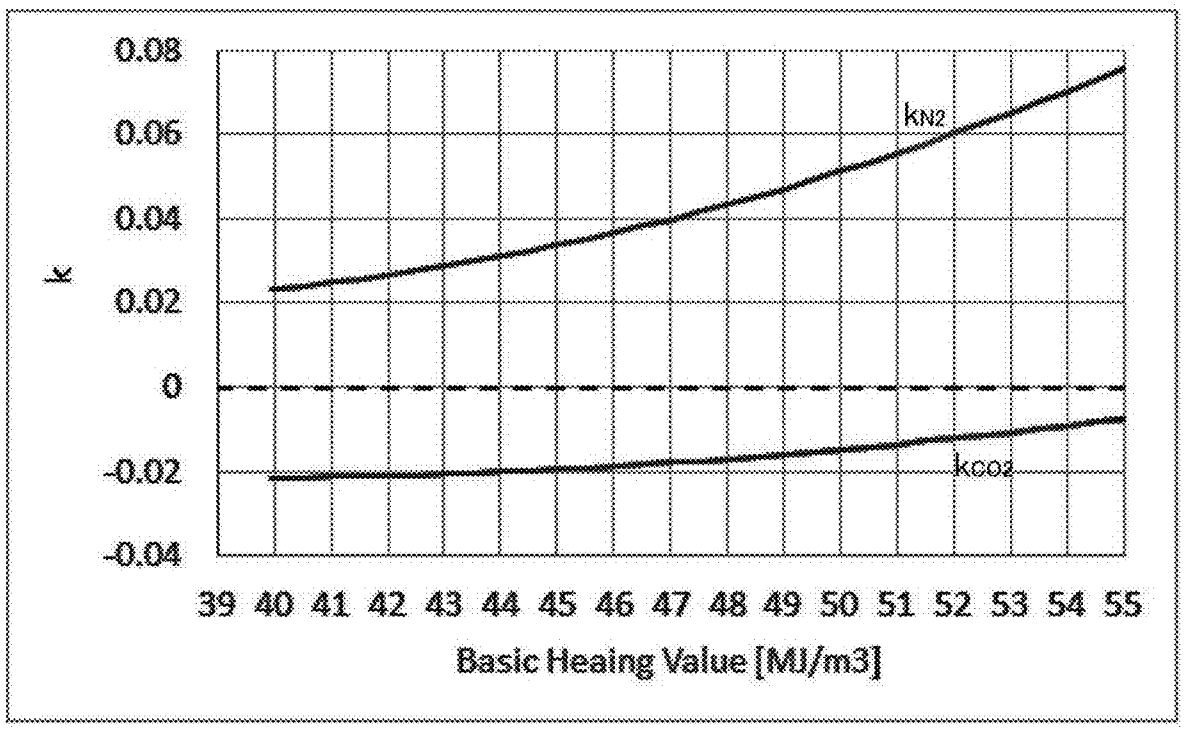
FIG. 8 is a graph comparing correction coefficients that correct the influence of miscellaneous gases.

Here, attention is paid to the $N_2$ correction coefficient $k_{N2}$, the $CO_2$ correction coefficient $k_{CO2}$, and the miscellaneous gas correction coefficient k'. Considering an existing natural gas, the basic heating value thereof may be considered to be between 39.933 and 47 $MJ/m^3$ (around 55 $MJ/m^3$ at the highest). The applicant of the present invention examined possible values of the $N_2$ correction coefficient $k_{N2}$ in the formula (5.2) and the $CO_2$ correction coefficient $k_{CO2}$ in the formula (5.3) in this range of the basic heating value $H_{HC}$. The result thereof is shown in FIG. 8. In FIG. 8, the horizontal axis represents the basic heating value $H_{HC}$, and the vertical axis represents the correction coefficients $k_{N2}$ and $k_{CO2}$.

As a result, the $N_2$ correction coefficient $k_{N2}$ takes positive values and the $CO_2$ correction coefficient $k_{CO2}$ takes negative values in the range of the above-described basic heating value. This means that the normalized compression factor $N(x_{N2}, x_{CO2})$ becomes larger as the nitrogen gas concentration $x_{N2}$ increases, and that the normalized compression factor $N(x_{N2}, x_{CO2})$ becomes smaller as the carbon dioxide gas concentration $x_{CO2}$ increases.

Meanwhile, since the miscellaneous gas correction coefficient k' in the formula (10) is a value selected with reference to the $N_2$ correction coefficient $k_{N2}$ of the formula (5.2), the miscellaneous gas correction coefficient k' constantly takes positive values. This means that the term $(k' \times x_{N2})$ and the term $(1.56\ k' \times x_{CO2})$ in the formula (10) both take positive values, and therefore the miscellaneous gas correction coefficient k' of the formula (10) cannot cause the normalized compression factor N to be smaller (to be negative) when the carbon dioxide gas concentration $x_{CO2}$ increases, unlike the $CO_2$ correction coefficient $k_{CO2}$.

However, the virtual basic heating value $H'_{HC}$ not including (excluding) miscellaneous gas components is originally calculated reversely from the miscellaneous gas total approximate concentration y on the basis of the natural gas heating value (gross heating value) Hs obtained from the Opt-Sonic arithmetic operation by using the formula (9). Accordingly, when the carbon dioxide gas concentration $x_{CO2}$ is 0 mol %, the miscellaneous gas total approximate concentration y totally coincides with the nitrogen gas concentration $x_{N2}$, so that the virtual basic heating value $H'_{HC}$ becomes equal to the basic heating value $H_{HC}$ of the formula (6). However, when the carbon dioxide gas concentration $x_{CO2}$ is larger than 0 mol %, the carbon dioxide gas concentration $x_{CO2}$ included in the miscellaneous gas total approximate concentration y used in the reverse calculation is increased by 1.56 times. Accordingly, the virtual basic heating value $H'_{HC}$ has the tendency of shifting in the direction of becoming larger than the basic heating value $H_{HC}$ as the carbon dioxide gas concentration $x_{CO2}$ increases. As is clear from FIGS. 7(A)-7(D), the normalized compression factor N becomes lower as the basic heating value $H_{HC}$ is higher. Accordingly, a virtual normalized compression factor $N'_{HC}$ of the formula (10.1) corresponding to the first term of the formula (10) becomes smaller than the normalized compression factor $N_{HC}$ of the formula (5.1) corresponding to first term of the formula (5).

Meanwhile, as for the miscellaneous gas total approximate concentration y used in the second term of the formula (10), the carbon dioxide gas concentration $x_{CO2}$ included therein is made 1.56 times larger than an actual value. At the same time, the coefficient k' used in the second term includes the virtual basic heating value $H'_{HC}$ in the first term and the second term as shown in the formula (10.2). Accordingly, the virtual basic heating value $H'_{HC}$ has the property of shifting in the direction of becoming larger than the basic heating value $H_{HC}$ as the carbon dioxide gas concentration $x_{CO2}$ is larger as described above, and therefore when a carbon dioxide gas is included, $k' \times y$ in the second term of the formula (10) becomes larger than the sum of the second term and the third term of the formula (5).

Therefore, when the formula (5) and the formula (10) are compared as a whole, the first term of the formula (10) becomes smaller than the first term of the formula (5), whereas $k' \times y$ in the second term of the formula (10) becomes larger than the sum of the second term and the third term of the formula (5). As a result, it was expected that the formula (10) has the tendency of approaching (not significantly deviating from) the calculation result of the formula (5) due to an offset of the increase in the first term and the decrease in the second term. Therefore, it was considered that appropriately adjusting the first term and the second term of the formula (10) (offsetting the values thereof) can produce the miscellaneous gas correction coefficient k', which can cause the virtual normalized compression factor $N'_{HC}$ to be smaller (to be negative) when the carbon dioxide gas concentration $x_{CO2}$ increases. Hence, in the formula (10.2), it was examined to use an adjustment coefficient D (by multiplying coefficients $a_{N2}$, $b_{N2}$, and $c_{N2}$ of the respective right terms of the formula (5.2) by the adjustment coefficient D) so as to reduce an error between the result of arithmetic operation by the formula (5) and that by the formula (10) by appropriately selecting the adjustment coefficient D.

The applicant of the present invention performed a simulation to compare the compression factor calculated using ISO12213-3 and the compression factor calculated on the basis of the normalized compression factor N which is calculated (by the formula (10)) using the Opt-Sonic arithmetic operation, for natural gases having various compositions of a carbon dioxide and a nitrogen gas.

As a result, a value (for example, 0.85) that can suppress an error from the compression factor calculated using ISO12213-3 to be small was selected as the adjustment coefficient D of the formula (10.2) for both the natural gas with a high amount of a carbon dioxide gas and the natural gas with a high amount of a nitrogen gas.

Although the adjustment coefficient D is 0.85 in the above-described example, the adjustment coefficient D is not limited thereto, and appropriate values can be selected in accordance with the types of natural gases. For example, in the case of a gas that does not contain a carbon dioxide gas, such as an LNG vaporized gas, the adjustment coefficient D is desirably 1.0 (or values close to 1.0). In the case of a natural gas with the adjustment coefficient D=1, i.e., a gas not containing a carbon dioxide gas, the miscellaneous gas correction coefficient k' is equal to the $N_2$ correction coefficient $k_{N2}$, and the virtual basic heating value $H'_{HC}$ is equal to the basic heating value $H_{HC}$ in the formula (6). In the case of adding a biogas to a natural gas, the influence of the carbon dioxide gas concentration can be dominant, and therefore it is desirable to set the adjustment coefficient D to be low (for example, about 0.7). The adjustment coefficient D in the present embodiment is, for example, a value of $0.5 \leq D \leq 1.5$.

Thus, according to the calculation device and the calculation method of the present embodiment, it is possible to calculate the virtual basic heating value $H'_{HC}$ using the Opt-Sonic arithmetic operation and to calculate physical quantities (for example, the compression factor) relating to the state of a natural gas by using the virtual basic heating value $H'_{HC}$ as a substitute of the basic heating value $H_{HC}$. In that case, it is possible to calculate the miscellaneous gas correction coefficient k' that can cause the virtual normalized compression factor $N'_{HC}$ in the first term of the formula (10) to be smaller (to be negative) (by an appropriate offset of the first term and the second term of the formula (10)) in accordance with increase of the carbon dioxide gas concentration $x_{CO2}$. In the calculation of the miscellaneous gas correction coefficient k', using the adjustment coefficient D makes it possible to adjust the degree of offset between the first term and the second term of the formula (10) in accordance with the increase of the carbon dioxide gas concentration $x_{CO2}$. In addition, the adjustment coefficient D can be set and adjusted to an appropriate value (0.85 in this case). For example, the calculation device 1 of the present embodiment can hold the adjustment coefficient D as a preset value (for example, an initial value), or can receive an input of any adjustment coefficient D from the outside. In the program of the present embodiment, the adjustment coefficient D may be held as a preset value (a constant or an initial value), or the adjustment coefficient D may be one of the input parameters.

As a result, both the normalized compression factor N ($x_{N2}$, $x_{CO2}$) calculated by the formula (5) and the normalized compression factor N calculated by the formula (10) can produce equal values for the same type of natural gases under the same conditions.

<Generalization of Normalized Compression Factor>

In the case of converting the normalized compression factor N ($x_{N2}$, $x_{CO2}$) obtained by the formula (5) or the normalized compression factor N obtained by the formula (10) to a general formula Z(T, P) for the compression factor Z based on the pressure P and the temperature T, a conversion formula shown in the formula (11) below is used.

[Mathematical formula 11]

$$Z(T, P) = \boxed{-N^{46.547MJ}_{39.933MJ}(x_{N2}, x_{CO2})} \times (Z_{46.547MJ}(T, P) - Z_{39.933MJ}(T, P)) + Z_{39.933MJ}(T, P) \quad (11)$$

provided that $$Z_{39.933MJ}(T, P) = 1 + \sum_{m=1}^{6} \sum_{n=0}^{4} a_{m,n} T^n P^m \quad (11.1)$$

$$Z_{46.547MJ}(T, P) = 1 + \sum_{m=1}^{6} \sum_{n=0}^{4} b_{m,n} T^n P^m \quad (11.2)$$

Note that $a_{m,n}$, and $b_{m,n}$ included in the formula (11.1) and the formula (11.2) are coefficients determined by the heating values of gases A and B selected when the compression factor is normalized. In the present embodiment, the coefficients correspond to the gas A of 39.933 MJ/m$^3$ (CH4=100%) and the gas B of 46.547 MJ/m$^3$ (CH4:C2H6:C3H8:C4H10=86:8:4:2). In this case, the coefficient $a_{m,n}$ is a value shown in Table 1 below, and the coefficient $b_{m,n}$ is a value shown in Table 2 below.

TABLE 1

| | $a_{m,n}$ | | | | |
|---|---|---|---|---|---|
| | n | | | | |
| m | 0 | 1 | 2 | 3 | 4 |
| 1 | $-2.35036 \times 10^{-2}$ | $2.87327 \times 10^{-4}$ | $-1.64352 \times 10^{-6}$ | $3.42170 \times 10^{-9}$ | $6.25526 \times 10^{-12}$ |
| 2 | $-5.32383 \times 10^{-5}$ | $1.05061 \times 10^{-5}$ | $-2.89761 \times 10^{-7}$ | $5.07148 \times 10^{-9}$ | $-3.64105 \times 10^{-11}$ |
| 3 | $1.96841 \times 10^{-5}$ | $-1.22527 \times 10^{-6}$ | $7.20498 \times 10^{-8}$ | $-1.77551 \times 10^{-9}$ | $1.42934 \times 10^{-11}$ |
| 4 | $-1.39998 \times 10^{-5}$ | $2.74477 \times 10^{-7}$ | $-1.66331 \times 10^{-8}$ | $3.93329 \times 10^{-10}$ | $-3.09583 \times 10^{-12}$ |
| 5 | $2.92517 \times 10^{-7}$ | $-3.10250 \times 10^{-8}$ | $1.57764 \times 10^{-9}$ | $-3.54783 \times 10^{-11}$ | $2.74550 \times 10^{-13}$ |
| 6 | $-1.03879 \times 10^{-8}$ | $9.51030 \times 10^{-10}$ | $-4.63848 \times 10^{-11}$ | $1.03507 \times 10^{-12}$ | $-8.00392 \times 10^{-15}$ |

TABLE 2

| | $b_{m,n}$ | | | | |
|---|---|---|---|---|---|
| | n | | | | |
| m | 0 | 1 | 2 | 3 | 4 |
| 1 | $-3.45532 \times 10^{-2}$ | $3.53753 \times 10^{-4}$ | $-2.12257 \times 10^{-7}$ | $-2.96449 \times 10^{-8}$ | $2.18618 \times 10^{-10}$ |
| 2 | $-1.12462 \times 10^{-3}$ | $9.73014 \times 10^{-5}$ | $-3.79388 \times 10^{-6}$ | $7.08069 \times 10^{-8}$ | $-4.83187 \times 10^{-10}$ |
| 3 | $3.10569 \times 10^{-4}$ | $-3.86076 \times 10^{-5}$ | $1.82219 \times 10^{-8}$ | $-3.82960 \times 10^{-8}$ | $2.79044 \times 10^{-10}$ |
| 4 | $-6.34425 \times 10^{-5}$ | $8.04882 \times 10^{-5}$ | $-4.18906 \times 10^{-7}$ | $9.12908 \times 10^{-9}$ | $-6.83021 \times 10^{-11}$ |
| 5 | $6.13475 \times 10^{-6}$ | $-7.50572 \times 10^{-7}$ | $4.01000 \times 10^{-8}$ | $-8.96848 \times 10^{-10}$ | $6.83158 \times 10^{-12}$ |
| 6 | $-1.86118 \times 10^{-7}$ | $2.34659 \times 10^{-8}$ | $-1.30916 \times 10^{-9}$ | $3.00693 \times 10^{-11}$ | $-2.32617 \times 10^{-13}$ |

The present embodiment is described in the case where the gas A is a gas (pure methane, a gas of $CH_4$=100%) with a heating value $H_{HC}$ of 39.933 MJ/$m^3$, and the gas B is a gas with a heating value $H_{HC}$ of 46.547 MJ/$m^3$ (a gas having a composition of $CH_4$:$C_2H_6$:$C_3H_8$:$C_4H_{10}$=86:8:4:2). However, without being limited thereto, any gases, such as gases available at the site can be adopted as the gas A and gas B. In that case, the coefficients $a_{m,n}$ and $b_{m,n}$ are prescribed values according to the adopted gases.

The calculation result of the formula (5) or the calculation result of the formula (10), or the result of output from the normalized compression factor calculation unit 151 (see FIG. 2(B)) of the calculation device 1 in the present embodiment is used as the value of the normalized compression factor N($x_{N2}$, $x_{CO2}$) in the first term (a dashed square frame) of the right side of the formula (11). The normalized compression factor N by the formula (10) can also be used as an equal value. Then, by substituting optional temperature T and pressure P into the formula (11), the natural gas compression factor Z under the conditions of the temperature T and the pressure P can be obtained.

Figure 9:
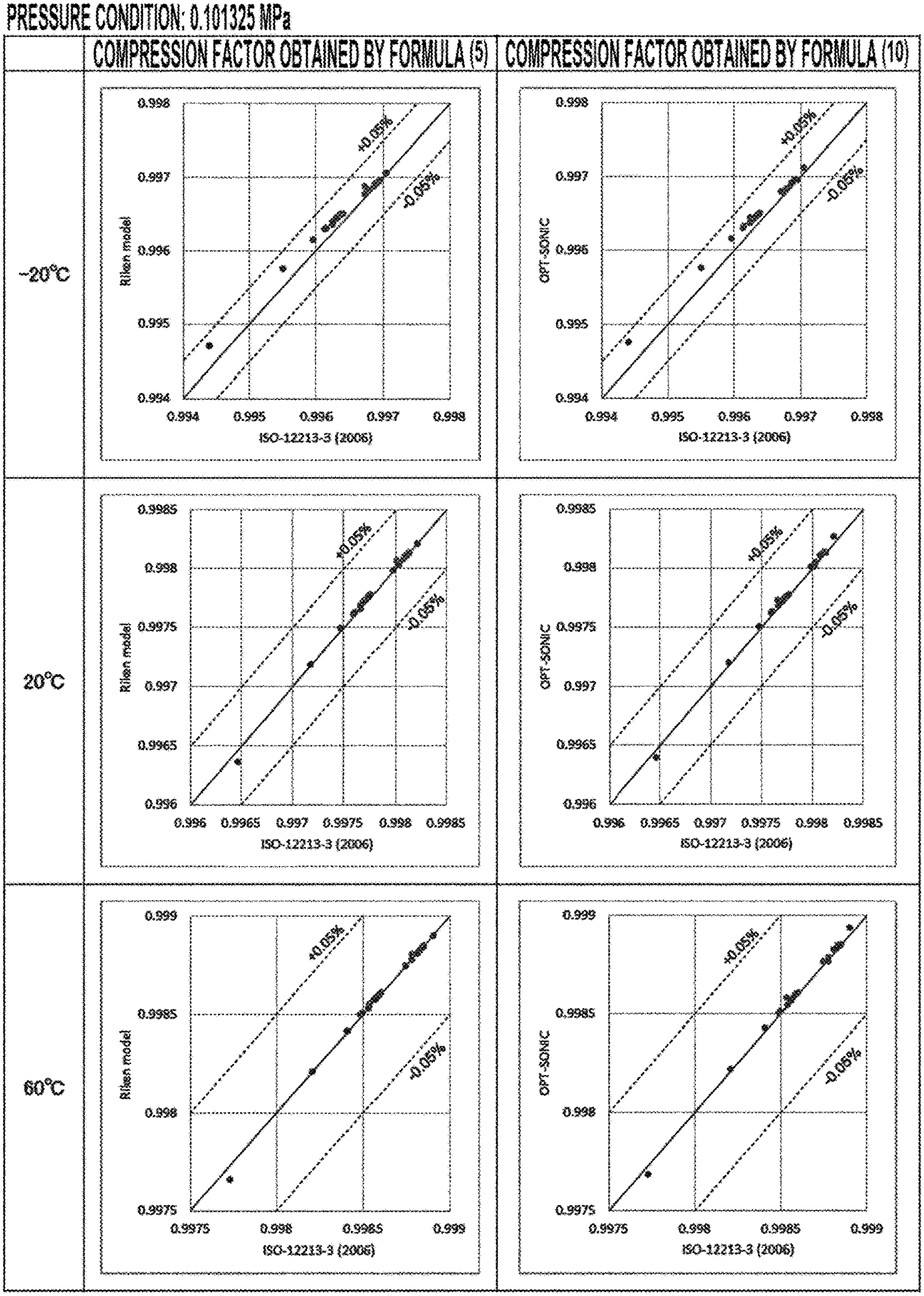
FIG. 9 includes graphs comparing the compression factors calculated by a conventional method and compression factors calculated by the method of the present embodiment.
Figure 10:
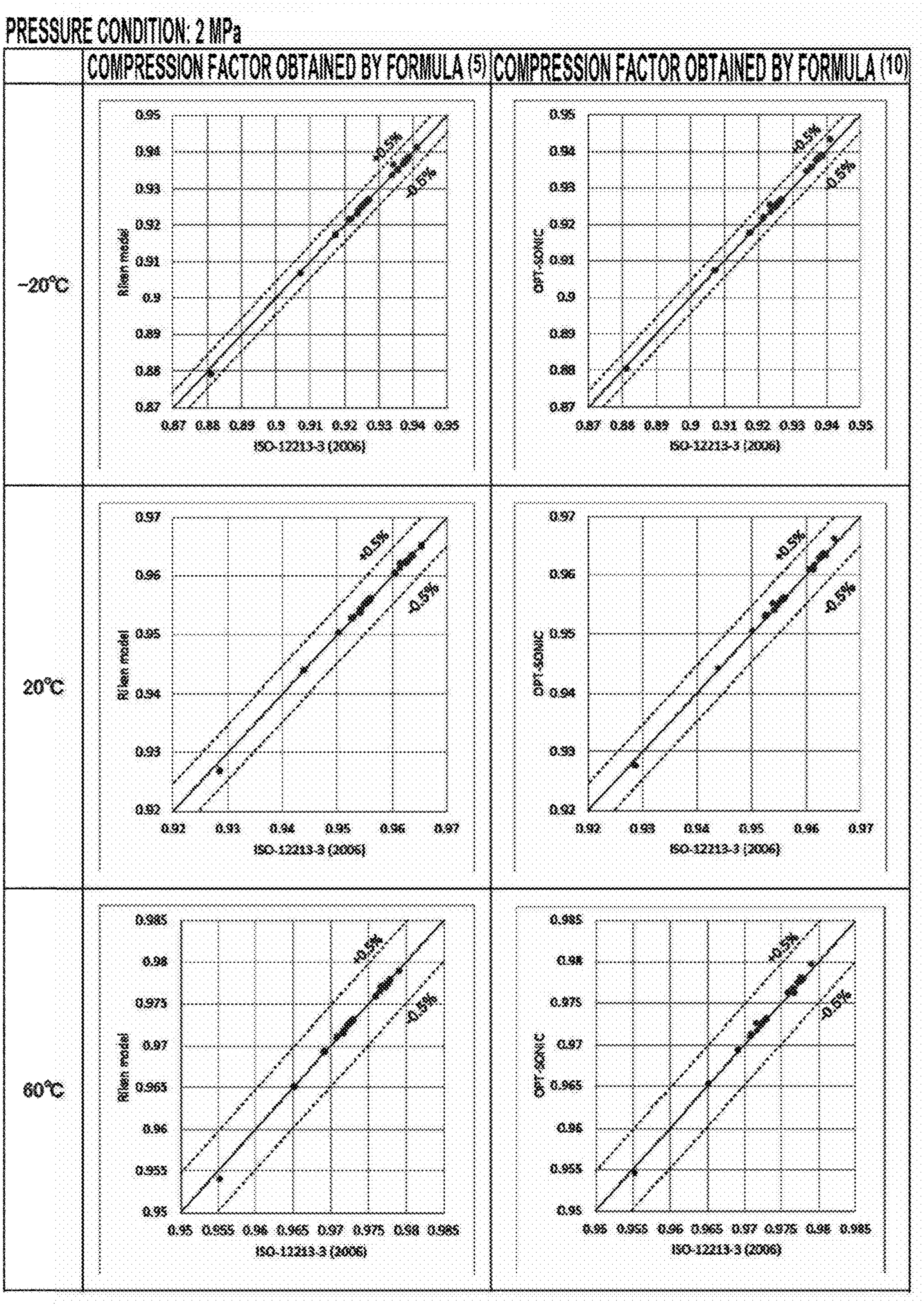
FIG. 10 includes graphs comparing the compression factors calculated by a conventional method and compression factors calculated by the method of the present embodiment.
Figure 11:
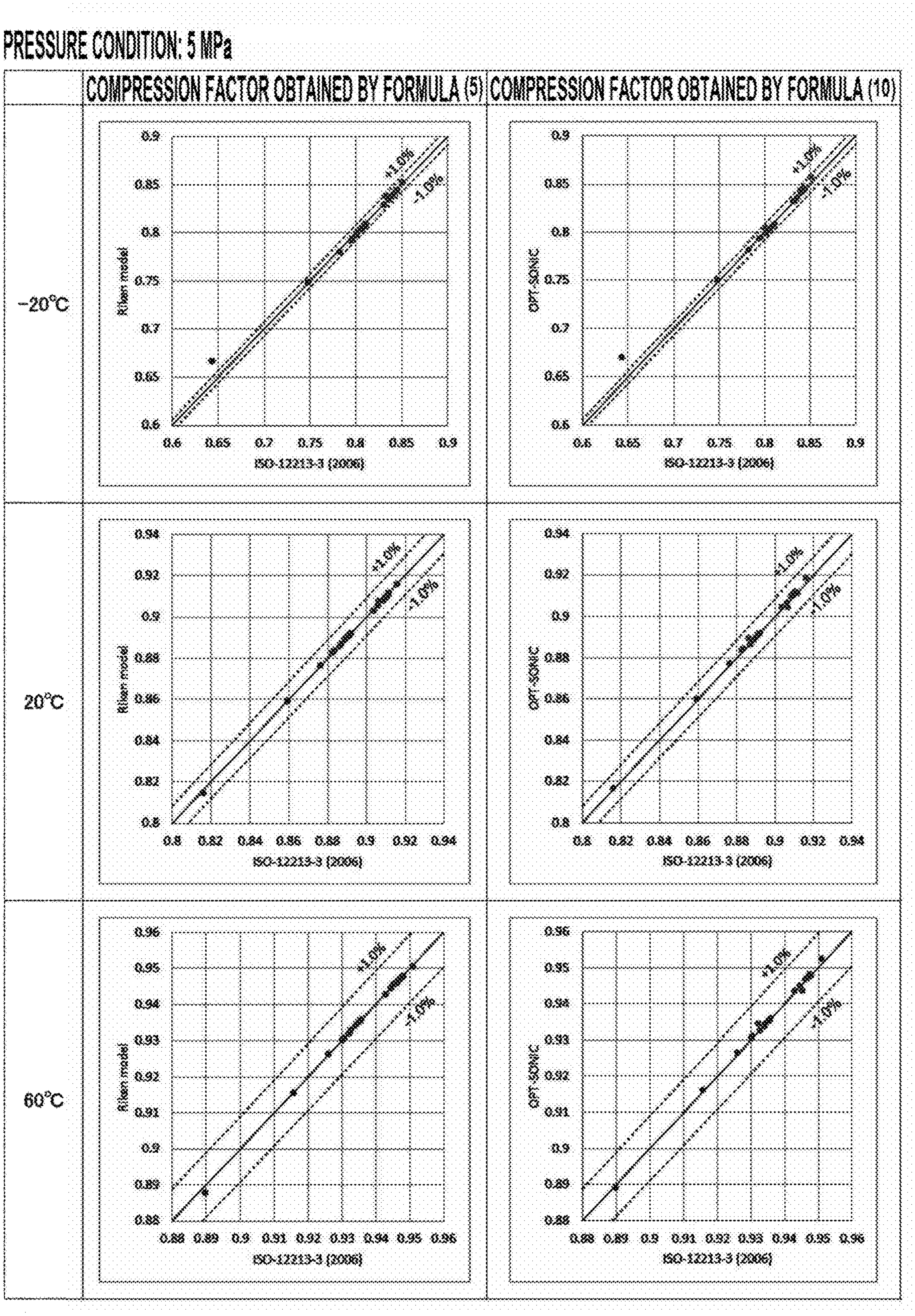
FIG. 11 includes graphs comparing the compression factors calculated by a conventional method and compression factors calculated by the method of the present embodiment.
Figure 12:
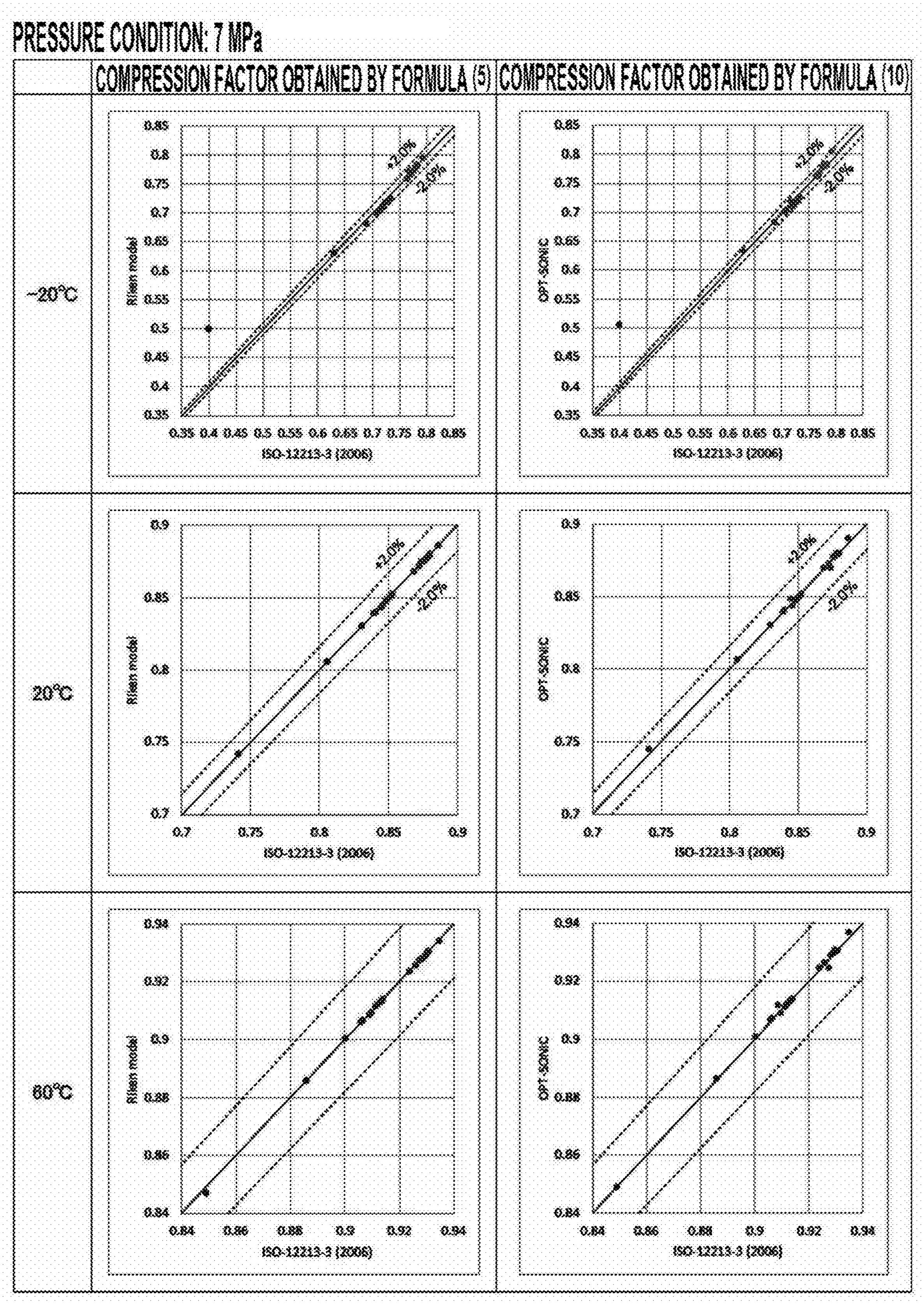
FIG. 12 includes graphs comparing the compression factors calculated by a conventional method and compression factors calculated by the method of the present embodiment.
Figure 13:
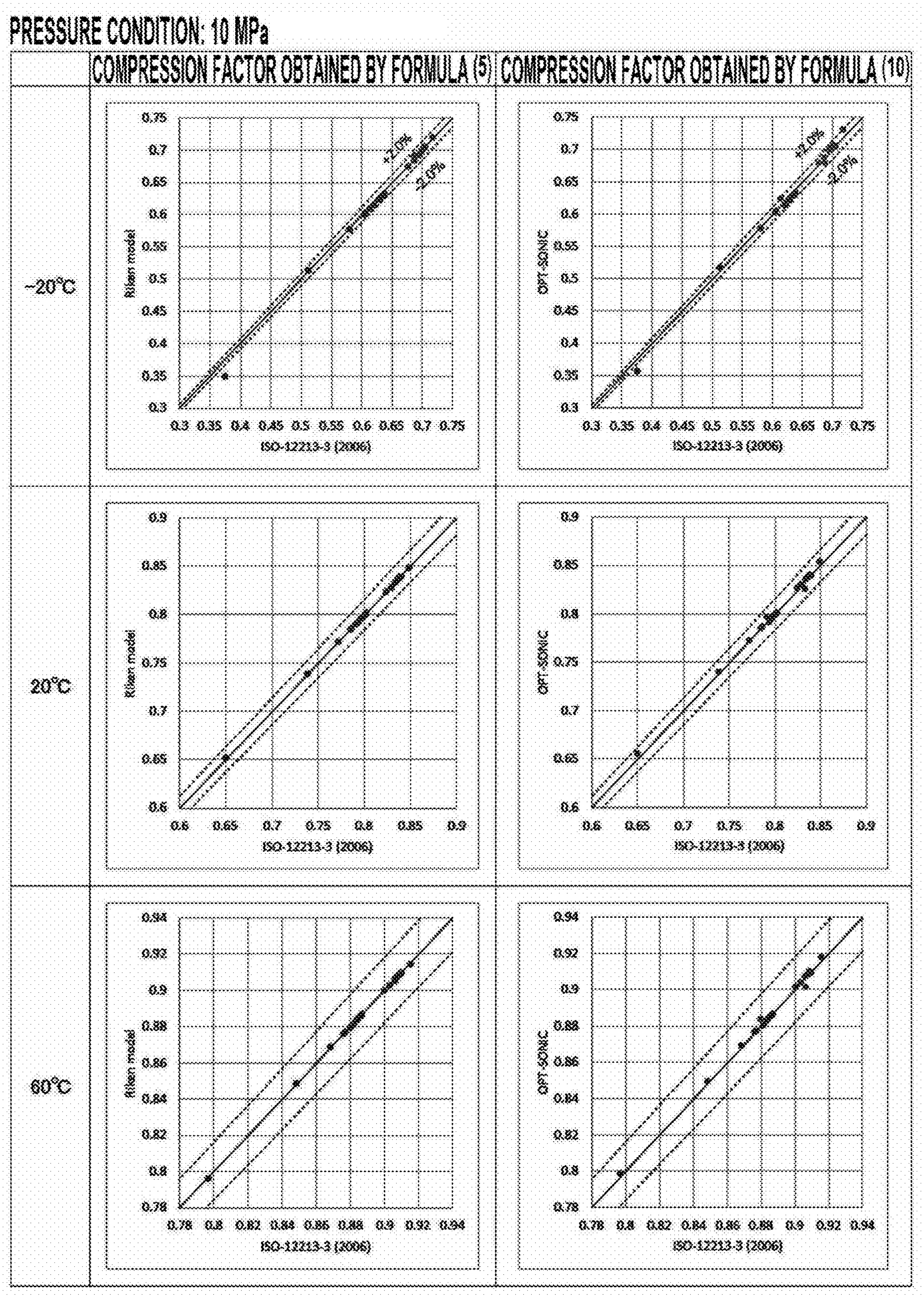
FIG. 13 includes graphs comparing the compression factors calculated by a conventional method and compression factors calculated by the method of the present embodiment.
Figure 14:
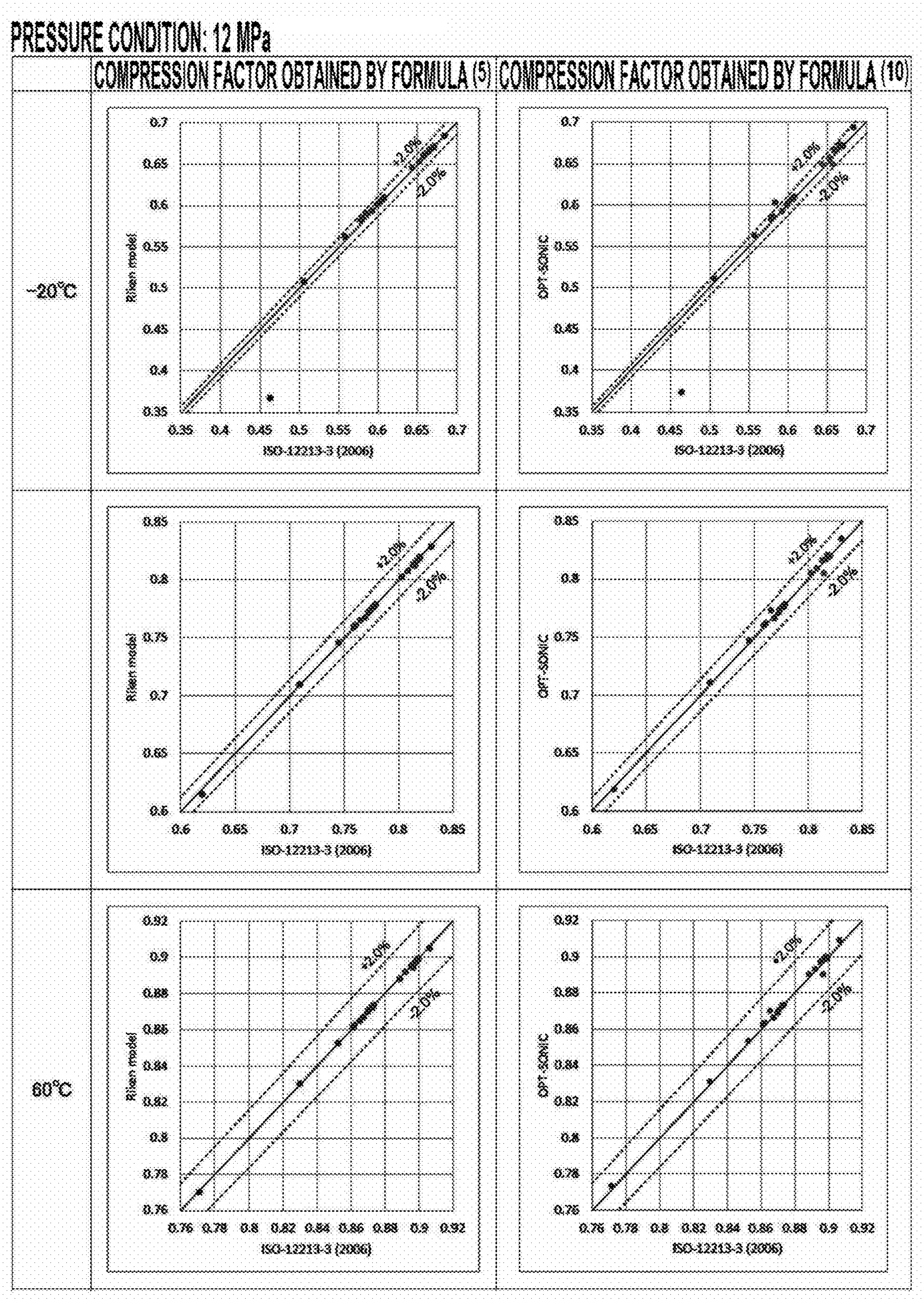
FIG. 14 includes graphs comparing the compression factors calculated by a conventional method and compression factors calculated by the method of the present embodiment.

FIG. 9 shows graphs comparing a compression factor obtained by the conventional calculation method according to ISO12213-3, a compression factor obtained by the formula (11) on the basis of the normalized compression factor N($x_{N2}$, $x_{CO2}$) calculated by the formula (5) of the present embodiment, and a compression factor obtained by the formula (11) on the basis of the normalized compression factor N calculated by the formula (10). The horizontal axis represents a compression factor Z obtained by the calculation method according to ISO12213-3. The vertical axis represents a compression factor Z obtained by the formula (11) on the basis of the normalized compression factor N($x_{N2}$, $x_{CO2}$) calculated by the formula (5) of the present embodiment and a compression factor Z obtained by the formula (11) on the basis of the normalized compression factor N calculated by the formula (10). The pressure (P) conditions were 0.101325 MPa (FIG. 9), 2 MPa (FIG. 10), 5 MPa (FIG. 11), 7 MPa (FIG. 12), 10 MPa (FIG. 13), and 12 MPa (FIG. 14). The temperature (T) conditions of −20° C., 20° C. and 40° C. for each of the pressure (P) conditions were used for calculation.

As a result of the calculations, it was found that the error from the calculation result of the compression factor according to ISO12213-3 falls within the range of i 0.05% to ±2.0% under different pressure P and temperature T conditions, and a high degree of agreement was thus demonstrated.

Thus, according to the present embodiment, by adopting the concept of the normalized compression factor N, the compression factor of a natural gas can be calculated simply and easily as compared to the conventional methods (calculation methods according to ISO12213-2 and ISO12213-3).

When the Opt-Sonic arithmetic operation is used to calculate the virtual basic heating value $H'_{HC}$ in particular, physical property values relating to the combustion or the state of a natural gas can be calculated. In particular, in the calculation of various physical property values (for example, the compression factor) that can be calculated using the basic heating value $H_{HC}$ of a natural gas, the virtual basic heating value $H'_{HC}$ can be used. In the above-described example, when the virtual basic heating value $H'_{HC}$ is used for the compression factor Z, which can be calculated by using the basic heating value $H_{HC}$, the number of input parameters used for the calculation can be reduced. In addition to the number of input parameters being reduced, the input parameters to be used are values easily acquired, such as the refractive index and the density of a natural gas (the values acquired by devices that are small, simple, inexpensive, and easy to handle). Accordingly, as compared to the case of using, for example, conventional analytical values of gas chromatography, physical property values (for example, the compression factor) can be calculated simply and easily.

Various physical property values that can be calculated using the basic heating value $H_{HC}$ are not limited to the compression factor. For example, even combustion speeds can be adopted in a similar manner. This will be described below.

<Calculation Method of Combustion Speed>

The applicant of the present invention verified how the compositions of a plurality of types of natural gases influence the basic heating value and the combustion speed (MCP). The natural gases used for verification are mixed gases composed only of three different types of paraffin-based hydrocarbon gases: a ($CH_4$-$C_2H_6$) gas, a ($CH_4$-$C_3H_8$) gas; and a ($CH_4$-$C_4H_{10}$) gas.

Figure 15B:
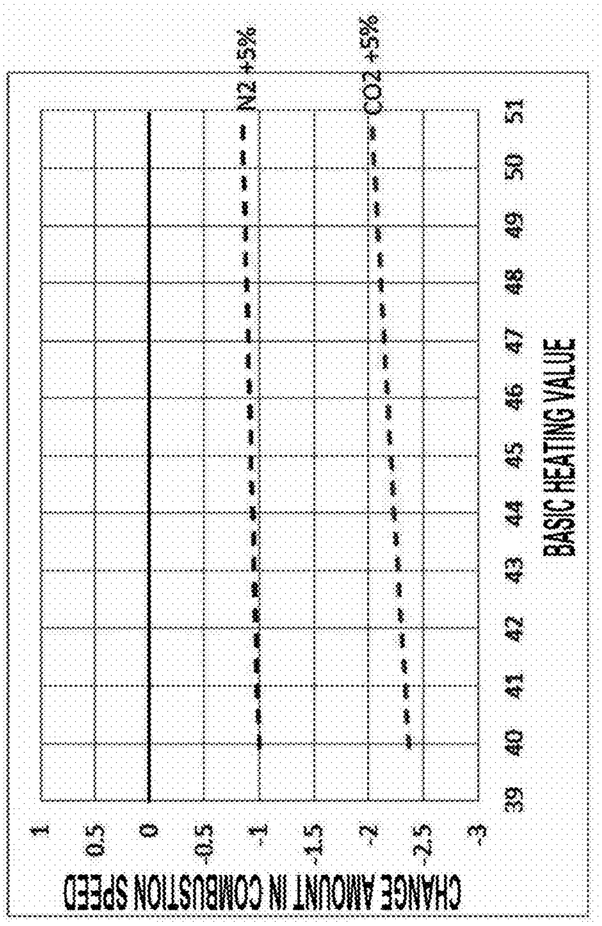
FIG. 15(B) is a graph indicating the relation between a change amount in combustion speed and the basic heating value of natural gases containing miscellaneous gas components.
Figure 15A:
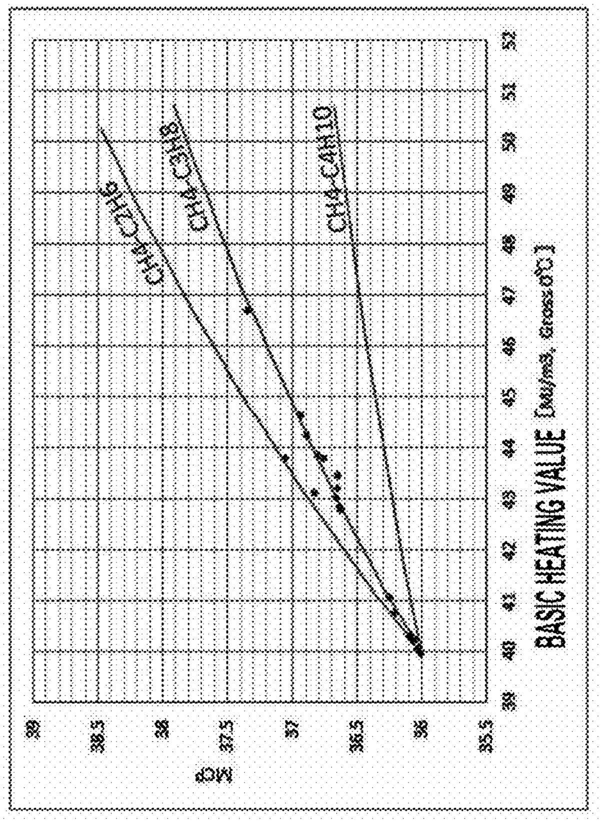
FIG. 15(A) is a graph showing the relation between a basic heating value (calculated value) and a combustion speed of a plurality of natural gases by an MCP calculation formula according to the conventional method.

FIG. 15(A) is a graph showing the relation between the basic heating values of the three types of mixed gases (calculated values based on ISO-6976) and the values by a calculation formula ((Pa) formula) of the combustion speed MCP using the analytical values of gas chromatography according to the conventional methods. The horizontal axis represents the basic heating value [MJ/$m^3$], and the vertical axis represents the combustion speed MCP. As a result, it was found that the correlation between the basic heating value and the MCP can be much different depending on the composition of natural gases (mixed gases).

However, as a result of performing similar verification of the correlation using existing natural gases (natural gases having compositions listed in ISO TR22302:2014, Table B.6, No. 1 to 24), the results of the relation between the basic heating value $H_{HC}$ and the combustion speed MCP showed the correlation close to that of the ($CH_4$-$C_3H_8$) gas. The results indicate that the combustion speed MCP of existing natural gases can be approximately expressed by the following formula (12).

[Mathematical formula 12]

$$MCP = -0.004637 \times H_{HC}^2 + 0.5961 \times H_{HC} + 19.5965 \quad (12)$$

As shown in FIG. 15(A), a mixed gas was formed by mixing the ($CH_4$-$C_3H_8$) gas as shown in FIG. 15(A) with 5 mol % nitrogen gas and 5 mol % carbon dioxide gas as miscellaneous gas components, and the relation between a change amount in combustion speed and the basic heating value of the mixed gas was verified with the ($CH_4$-$C_3H_8$) gas as a reference (0). The result is shown in FIG. 15(B). The result of the verification indicates that the change amount in combustion speed due to the miscellaneous gas components being mixed therein becomes larger with an increase in the basic heating value.

The result indicates that when a natural gas (an existing natural gas), having a basic heating value in the vicinity of the curve (FIG. 15(A)) of the reference ($CH_4$-$C_3H_8$) gas containing no miscellaneous gas components, is mixed with $x_{N2}$ [mol %] nitrogen gas and $x_{CO2}$ [mol %] carbon dioxide gas as miscellaneous gas components, the combustion speed can be expressed by the formula (13).

[Mathematical formula 13]

$$MCP = -0.004637 \times H_{HC}^2 + 0.5961 \times H_{HC} + 19.5965 + A \times x_{N2} + B \times x_{CO2} \quad (13)$$

provided that $$A = 0.00265438 \times H_{HC} - 0.30474328 \quad (13.1)$$

$$A = 0.0062857 \times H_{HC} - 072340434 \quad (13.2)$$

Note that the heating value $H_{HC}$ used in the formula (13) represents the basic heating value of a natural gas. Here, when the natural gas contains a nitrogen gas (the nitrogen gas concentration $x_{N2}$ [mol %]) and a carbon dioxide gas (the carbon dioxide gas concentration $x_{CO2}$ [mol %]) as miscellaneous gas components, the relation between the gross heating value Hs and the basic heating value $H_{HC}$ of the natural gas is expressed by the formula (14) below.

[Mathematical formula 14]

$$H_{HC} = H_S \times \frac{100}{100 - (x_{N2} + x_{CO2})} \quad (14)$$

Therefore, by the formula (14), the formula (13) functions as a formula for calculating the combustion speed on the basis of three input parameters, i.e., the heating value Hs of a natural gas, the carbon dioxide gas concentration $x_{CO2}$, and the nitrogen gas concentration $x_{N2}$. In other words, in the case of a natural gas containing miscellaneous gas components, it can be said that when the heating value (gross heating value) Hs of the natural gas, the carbon dioxide gas concentration $x_{CO2}$, and the nitrogen gas concentration $x_{N2}$ can be acquired, it is possible to calculate the basic heating value $H_{HC}$ by the formula (14) and to calculate the combustion speed MCP of the natural gas by the formula (13).

On the basis of this consideration, the combustion speed calculation method described with reference to FIG. 5(A) described above calculates the combustion speed MCP with three elements, i.e., the heating value (gross heating value) Hs of a natural gas, the carbon dioxide gas concentration $x_{CO2}$, and the nitrogen gas concentration $x_{N2}$ as input parameters, using the above-described formula (13) (and the formula (14)) as the normalized compression factor calculation formula.

The formula (13) (and the formula (14)) are formulas for calculating combustion speed (combustion speed calculation formulas) on the basis of three input parameters, i.e., the heating value Hs of a natural gas, the carbon dioxide molar concentration $x_{CO2}$, and the nitrogen molar concentration $x_{N2}$.

<Method of Arithmetic Operation of Opt-Sonic Combustion Speed>

Incidentally, in calculation of the combustion speed, the number of input parameters can be reduced by using the Opt-Sonic arithmetic operation, in exactly the same way as in the calculation of the compression factor. In addition, the virtual basic heating value $H'_{HC}$ can also be calculated in exactly the same way as in the calculation of the compression factor (the formulas (7) to (9) described above).

Even when the concentrations of miscellaneous gas components (the nitrogen gas concentration $x_{N2}$ and the carbon dioxide gas concentration $x_{CO2}$) are unknown, an arithmetic operation corresponding to the calculation of the combustion speed by the formula (13) is performed by the formula (15) below by substituting the virtual basic heating value $H'_{HC}$ for the basic heating value $H_{HC}$ of the formula (13). Therefore, the formula (15) is also a combustion speed calculation formula.

[Mathematical formula 15]

$$MCP = -0.004637 \times H'^2_{HC} + 0.5961 \times H'_{HC} + 19.5965 + C \times (x_{N2} + 1.56 \times x_{CO2}) \quad (15)$$

provided that $$C = 1.1 \times A = 1.1 \times (0.00265438 \times H'_{HC} - 0.30474328) \quad (15.1)$$

Here, when the formula (13) is compared to the formula (15), in the formula (13), a fourth term ($A \times x_{N2}$) and a fifth term ($B \times x_{CO2}$) of the right side are added as correction terms required due to the miscellaneous gas components being included. In the formula (15), a fourth term ($C \times (x_{N2} + 1.56 \times x_{CO2})$) of the right side is added as a correction term required due to the miscellaneous gas components being included. With reference to FIG. 15(B) again, in calculation of the combustion speed by the formula (13), as any of the nitrogen gas concentration $x_{N2}$ and the carbon dioxide gas concentration $x_{CO2}$ increases, the change amount in combustion speed tends to decrease. However, the influence of the carbon dioxide gas concentration $x_{CO2}$ on the change amount in combustion speed may be considered substantially twice the influence of the nitrogen gas concentration $x_{N2}$.

In the formula (15) using the Opt-Sonic arithmetic operation, the influence of the carbon dioxide gas concentration $x_{CO2}$ on the change amount in combustion speed is 1.56 times the influence of the nitrogen gas concentration $x_{N2}$ according to the fourth term of the right side. Therefore, it was considered that while there is a slight difference between the formula (13) and the formula (15), correcting the arithmetic operation by the formula (15) can provide a value substantially equal to the calculation result of the formula (13).

Accordingly, in the present embodiment, to make the calculation results of the combustion speed by the formula (13) and the formula (15) substantially equal to each other, C included in the correction term in the formula (15) was set to 1.1 times larger than A included in the correction term of the formula (13.1) (see the formula (15.1)).

For the value (referred to as "adjustment coefficient F") to be multiplied to A in the formula (15.1), a simulation was performed to compare the conventional calculation method of combustion speed (the method of obtaining a value on the basis of the (Pa) formula) and the calculation method of combustion speed using the Opt-Sonic arithmetic operation (the calculation method by the formula (15)) for natural gases with various gas compositions. As a result, a value that can reduce the error from the combustion speed calculated from the (Pa) formula, for both the natural gas with a high amount of a carbon dioxide gas and the natural gas with a high amount of a nitrogen gas, was selected as the adjustment coefficient F of the formula (15.1).

The adjustment coefficient F is 1.1 (F=1.1) in the above-described example. However, without being limited thereto, the adjustment coefficient F is an appropriate value (for example, $0.5 \leq F \leq 1.5$) in accordance with the types of natural gases.

Thus, according to the calculation device and the calculation method of the present embodiment, it is possible to calculate the virtual basic heating value $H'_{HC}$ using the Opt-Sonic arithmetic operation and to calculate physical quantities (for example, the combustion speed) relating to the combustion of a natural gas by using the virtual basic heating value $H'_{HC}$ and the adjustment coefficient F as a substitute of the basic heating value $H_{HC}$. In this case, the adjustment coefficient F can be set and adjusted to an appropriate value (1.1 in this case). For example, the calculation device 1 of the present embodiment can hold the adjustment coefficient F as a preset value (for example, an initial value), or can receive an input of any adjustment coefficient F from the outside. In the program of the present embodiment, the adjustment coefficient F may be held as a preset value (a constant or an initial value), or the adjustment coefficient F may be one of the input parameters.

As a result, both the combustion speed $MCP(x_{N2}, x_{CO2})$ calculated by the formula (13) and the combustion speed MCP calculated by the formula (15) can produce equal values for the same type of natural gases under the same conditions.

Figure 16A:
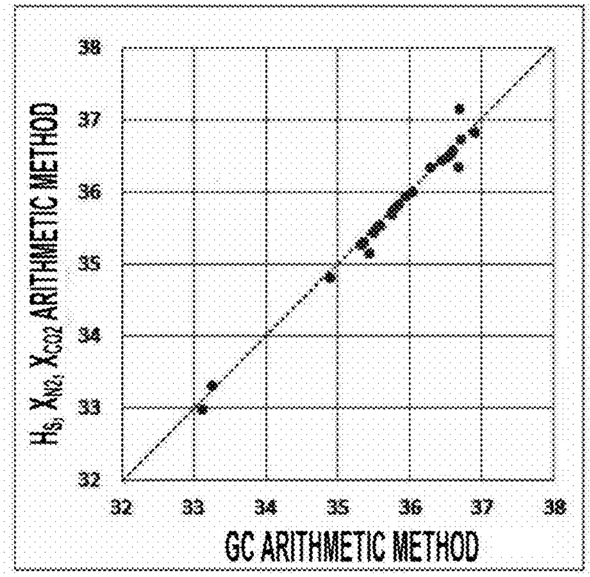
FIGS. 16(A) and 16(B) include graphs comparing the combustion speed calculated by the conventional method and the combustion speed calculated by the method of the present embodiment.
Figure 16B:
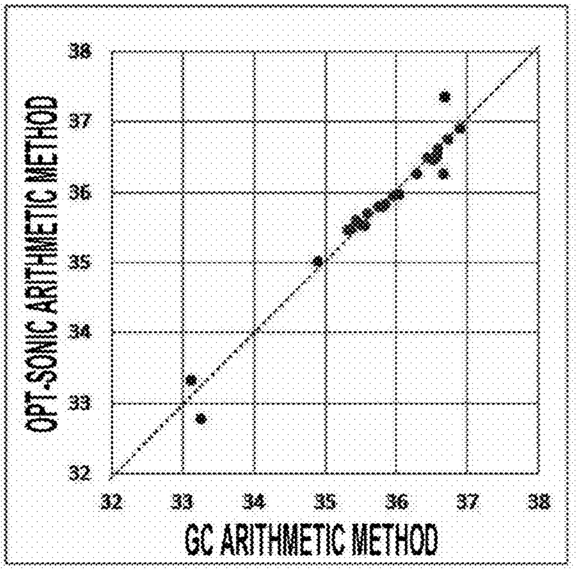

FIGS. 16(A) and 16(B) show graphs comparing the combustion speed calculated by the conventional (Pa) formula with the combustion speeds calculated by the formulas (13) and (15). In FIG. 16(A), the horizontal axis represents the combustion speed MCP obtained from the (Pa) formula, and the vertical axis represents the combustion speed MCP $(x_{N2}, x_{CO2})$ obtained from the formula (13). In FIG. 16(B), the horizontal axis represents the combustion speed MCP obtained from the (Pa) formula, and the vertical axis represents the combustion speed MCP obtained from the formula (15). The results of both calculations agreed with the combustion speed calculated by the conventional (Pa) formula with high accuracy.

As described in the foregoing, in the present embodiment, in calculation of the physical property values relating to a natural gas not containing, or containing a negligible amount of, hydrogen and carbon monoxide, the Opt-Sonic arithmetic operation is used to calculate the virtual basic heating value $H'_{HC}$, so that a plurality of different physical property values (for example, the compression factor, and the combustion speed), calculated on the basis of the basic heating value $H_{HC}$, can easily be calculated. For example, in general, the compression factor was conventionally calculated by the calculation methods according to ISO12213-2, ISO12213-3, or the like, and the combustion speed was calculated by the method as represented by the (Pa) formula. In these methods, the types and the number of input parameters were independently set, and therefore it was necessary to acquire (prepare) input parameters for each physical property value. Therefore, depending on the input parameters, measuring devices, analyzers, and the like were required, which caused inconvenience.

According to the present embodiment, different physical property values can be acquired by using a common calculation device and calculation method up to the stage (step) of calculating the virtual basic heating value $H'_{HC}$. The input parameters in particular are two elements of the refractive index and the density of a natural gas, and the devices for acquiring these parameters are smaller, simpler, and relatively more inexpensive than gas chromatography devices. Even in the case of calculating a plurality of different physical property values, a common device and method can be used up to the calculation of the virtual basic heating value $H'_{HC}$. Therefore, highly convenient, simple, and easy calculation can be achieved.

In the present embodiment, in calculation of the physical property values relating to a natural gas not containing, or containing a negligible amount of, hydrogen and carbon monoxide, the normalized compression factor N is calculated on the basis of three input parameters, i.e., the heating value Hs of the natural gas (a gross heating value converted to a measurement reference state temperature of 0° C., a combustion reference state of 0° C., and 101.325 kPa), the carbon dioxide gas concentration $x_{CO2}$, and the nitrogen gas concentration $x_{N2}$. Then, on the basis of the normalized compression factor N and the compression factor general formula (Z(T, P)) with the temperature T and the pressure P as parameters, the compression factor Z is calculated under the conditions of the pressure P and the temperature T to be required.

This can significantly reduce the input parameters compared to the conventional calculation methods according to ISO12213-2 and ISO12213-3. In the calculation methods according to ISO12213-2 and ISO12213-3, the pressure P and the temperature T were used as initial input data. When the compression factor was calculated under the conditions of different temperatures and pressures, all the input data required for the respective calculation methods needed to be re-calculated, and this caused a problem of inconvenience. When the temperature or pressure was not measurable, there was also a problem that numerical values relating to the compression factor could not be acquired.

According to the present embodiment, the normalized compression factor N is calculated, and the normalized compression factor N is converted to a general formula for calculating the compression factor (function Z(T, P)). Accordingly, when the compression factor Z is calculated under the conditions of different temperatures and pressures, various compression factors Z can be calculated by changing only the input parameters, the temperature T and the pressure P in the general formula (function Z(T, P)).

In addition, calculating the normalized compression factor N using the Opt-Sonic arithmetic operation can reduce the input parameters to two elements of the refractive index and the density of a natural gas. The measurement of both the refractive index and the density can also be implemented with simpler, smaller, and less expensive devices than the conventional gas chromatography devices, so that the devices are also easy to handle.

In the present embodiment, the combustion speed relating to a natural gas, not containing, or containing a negligible amount of, hydrogen and carbon monoxide, can be calculated on the basis of three input parameters, i.e., the heating value Hs of a natural gas (a gross heating value converted to a measurement reference state temperature of 0° C., a combustion reference state of 0° C., and 101.325 kPa), the carbon dioxide gas concentration $x_{CO2}$, and the nitrogen gas concentration $x_{N2}$.

This can significantly reduce the input parameters compared to the conventional calculation method according to the (Pa) formula.

Furthermore, calculating the normalized compression factor N using the Opt-Sonic arithmetic operation can reduce the input parameters to two elements of the refractive index and the density of a natural gas. In addition, the measurement of both the refractive index and the density can be implemented with simpler, smaller, and less expensive devices than the conventional gas chromatography devices, so that the devices are also easy to handle.

The present invention is not limited to the embodiments described above, and various modifications can be made without departing from the scope and technical ideas of the present invention.

For example, in the embodiments described above, an example of calculating the heating value Hs using the arithmetic formula of the converted heating value (Opt-Sonic arithmetic formula) shown in the formula (7) has been described. However, the heating value Hs may be acquired by other known methods (arithmetic operations).

In the embodiment described above, the case where the necessity of measuring miscellaneous gas concentrations (the nitrogen gas concentration $x_{N2}$ and the carbon dioxide gas concentration $x_{CO2}$) is eliminated by using the Opt-Sonic arithmetic formula has been described as an example. However, at least one of the miscellaneous gases may separately be acquired (measured, for example) and then the various arithmetic operations may be performed.

For example, the target gas may also be an LNG vaporized gas or a biogas. In addition, the physical property values may include a "soot function" or an "incomplete combustion index". The miscellaneous gases are not limited to a nitrogen gas and a carbon dioxide gas. Similar arithmetic operations can be performed, and similar effects can be demonstrated with any miscellaneous gases as long as their types are limited.

The invention claimed is:

1. A calculation device configured to calculate a value relating to a combustible target gas containing miscellaneous gas components, the calculation device comprising:

a heating value calculation unit configured to calculate a heating value of the target gas on a basis of converted heating values obtained from a refractive index and a density of the target gas, respectively;

a miscellaneous gas total approximate-concentration calculation unit configured to calculate a total approximate concentration of the miscellaneous gas components on a basis of the converted heating values; and a virtual basic-heating-value calculation unit configured to calculate, on a basis of the heating value and the approximate concentration, a virtual basic heating value of the target gas when the miscellaneous gas components are assumed to be removed.

2. The calculation device according to claim 1, further comprising:

a refractive index-converted heating value acquisition unit capable of acquiring the converted heating value obtained from the refractive index of the target gas; and a density-converted heating value acquisition unit capable of acquiring the converted heating value obtained from the density of the target gas.

3. The calculation device according to claim 1, wherein the target gas is a natural gas, and the miscellaneous gas components mainly include nitrogen and carbon dioxide.

4. The calculation device according to claim 1, further comprising a physical property value calculation unit configured to calculate a physical property value of the target gas using the virtual basic heating value.

5. The calculation device according to claim 4, wherein the physical property value calculation unit performs error correction corresponding to the miscellaneous gas components.

6. The calculation device according to claim 4, wherein the physical property value is a compression factor.

7. The calculation device according to claim 6, wherein the compression factor is calculated on a basis of a normalized compression factor.

8. The calculation device according to claim 4, wherein the physical property value is a combustion speed.

9. A calculation method for causing a computer to execute a program to calculate a value relating to a combustible target gas containing miscellaneous gas components, the calculation method comprising executing on the computer the steps of:

a step of acquiring converted heating values obtained from a refractive index and a density of the target gas, respectively;

a step of calculating a heating value of the target gas on a basis of the converted heating values;

a step of calculating a total approximate concentration of the miscellaneous gas components on a basis of the converted heating values; and a step of calculating, on a basis of the heating value and the total approximate concentration, a virtual basic heating value of the target gas when the miscellaneous gas components are assumed to be removed.

10. The calculation method according to claim 9, further comprising:

a step of acquiring the converted heating value obtained from the refractive index of the target gas; and a step of acquiring the converted heating value obtained from the density of the target gas.

11. The calculation method according to claim 9, wherein the target gas is a natural gas, and the miscellaneous gas components mainly include nitrogen and carbon dioxide.

12. The calculation method according to claim 9, further comprising a step of calculating a physical property value of the target gas using the virtual basic heating value.

13. The calculation method according to claim 12, wherein, when the physical property value is calculated, error correction corresponding to the miscellaneous gas components is performed.

14. The calculation method according to claim 12, wherein the physical property value is a compression factor.

15. The calculation method according to claim 14, wherein the compression factor is calculated after a normalized compression factor is calculated.

16. The calculation method according to claim 12, wherein the physical property value is a combustion speed.

17. A non-transitory computer readable medium storing the program for causing the computer to execute the calculation method according to claim 9.

18. The calculation device according to claim 5, wherein the physical property value is a compression factor.

19. The calculation device according to claim 18, wherein the compression factor is calculated on a basis of a normalized compression factor.

20. The calculation device according to claim 5, wherein the physical property value is a combustion speed.

* * * * *